(12) United States Patent  (10) Patent No.: US 7,985,254 B2
Tolkowsky  (45) Date of Patent: Jul. 26, 2011

(54) ENDOBRONCHIAL FLUID EXHALER DEVICES AND METHODS FOR USE THEREOF

(76) Inventor: David Tolkowsky, Tel Aviv (IL)

(*) Notice: Subject to any disclaimer, the term of this patent is extended or adjusted under 35 U.S.C. 154(b) by 282 days.

(21) Appl. No.: 12/006,950

(22) Filed: Jan. 8, 2008

(65) Prior Publication Data

US 2008/0167614 A1    Jul. 10, 2008

Related U.S. Application Data

(60) Provisional application No. 60/879,392, filed on Jan. 8, 2007, provisional application No. 60/906,200, filed on Mar. 12, 2007.

(51) Int. Cl.
*A61F 2/04* (2006.01)
(52) U.S. Cl. .................. 623/9; 128/200.24; 623/23.65
(58) Field of Classification Search ........... 623/9, 23.65; 128/204.24, 200.24; 604/131; 600/16
See application file for complete search history.

(56) References Cited

U.S. PATENT DOCUMENTS

| | | | |
|---|---|---|---|
| 3,470,876 A | 10/1969 | Barchilon | |
| 3,826,265 A | 7/1974 | Giori et al. | |
| 4,017,858 A | 4/1977 | Kuipers | |
| 4,313,431 A | 2/1982 | Frank | |
| 4,615,332 A | 10/1986 | Buess et al. | |
| 4,849,692 A | 7/1989 | Blood | |
| 5,156,154 A | 10/1992 | Valenta, Jr. et al. | |
| 5,325,845 A | 7/1994 | Adair | |
| 5,372,587 A | 12/1994 | Hammerslag et al. | |
| 5,553,611 A | 9/1996 | Budd et al. | |
| 5,558,091 A | 9/1996 | Acker et al. | |
| 5,611,335 A | 3/1997 | Makhoul et al. | |
| 5,697,377 A | 12/1997 | Wittkampf | |
| 5,744,953 A | 4/1998 | Hansen | |
| 5,972,026 A | 10/1999 | Laufer | |
| 6,063,085 A | 5/2000 | Tay et al. | |
| 6,165,164 A | 12/2000 | Hill et al. | |
| 6,233,476 B1 | 5/2001 | Strommer et al. | |
| 6,258,100 B1 | 7/2001 | Alferness et al. | |
| 6,283,988 B1 | 9/2001 | Laufer et al. | |
| 6,293,951 B1 | 9/2001 | Alferness et al. | |
| 6,445,943 B1 | 9/2002 | Ferre et al. | |
| 6,490,474 B1 | 12/2002 | Willis et al. | |
| 6,593,884 B1 | 7/2003 | Gilboa et al. | |
| 6,636,757 B1 | 10/2003 | Jacob et al. | |
| 6,679,264 B1 | 1/2004 | Deem et al. | |

(Continued)

FOREIGN PATENT DOCUMENTS

WO    WO 2005/074380    8/2005

OTHER PUBLICATIONS

Stock et al., "Development and application of a real-time monitoring and feedback system for deep inspiration breath hold based on external marker tracking", Med Phys. Aug. 2006; 33(8):2868-77—an abstract.

(Continued)

*Primary Examiner* — Thomas J Sweet
*Assistant Examiner* — Yashita Sharma
(74) *Attorney, Agent, or Firm* — Husch Blackwell LLP

(57) ABSTRACT

Apparatus is provided, including a first rotating member configured to be implanted in an airway of a subject and rotated in an inhalation direction by an inhaled flow of fluid in the airway. A mechanical energy accumulator is configured to accumulate energy from the rotation of the first rotating member. Other embodiments are also described.

15 Claims, 10 Drawing Sheets

U.S. PATENT DOCUMENTS

| | | |
|---|---|---|
| 6,690,963 B2 | 2/2004 | Ben-Haim et al. |
| 6,694,979 B2 | 2/2004 | Deem et al. |
| 6,757,563 B2 | 6/2004 | Sweeney |
| 6,783,536 B2 | 8/2004 | Vilsmeier et al. |
| 6,784,660 B2 | 8/2004 | Ashe |
| 6,836,745 B2 | 12/2004 | Seiler et al. |
| 6,947,788 B2 | 9/2005 | Gilboa et al. |
| 6,990,427 B2 | 1/2006 | Kirsch et al. |
| 6,994,094 B2 | 2/2006 | Schwartz |
| 7,115,127 B2 | 10/2006 | Lindenbaum et al. |
| 7,130,700 B2 | 10/2006 | Gardeski et al. |
| 7,189,240 B1 | 3/2007 | Dekel |
| 2003/0127090 A1 | 7/2003 | Gifford et al. |
| 2004/0106880 A1 | 6/2004 | Weng et al. |
| 2004/0158294 A1 | 8/2004 | Thompson |
| 2004/0237966 A1 | 12/2004 | Tanaka |
| 2005/0015866 A1 | 1/2005 | Steinert |
| 2005/0025816 A1 | 2/2005 | Tanaka |
| 2005/0103340 A1 | 5/2005 | Wondka |
| 2005/0171508 A1 | 8/2005 | Gilboa |
| 2006/0161233 A1 | 7/2006 | Barry et al. |
| 2006/0178552 A1 | 8/2006 | Gross |
| 2006/0276775 A1 | 12/2006 | Rosenberg et al. |

OTHER PUBLICATIONS

Wilmot C. Ball Jr., "Interactive respiratory physiology", MD, Johns Hopkins School of Medicine, Office of Medical Informatics Education, 1996.

Tsuda et al., "Chaotic mixing deep in the lung", Proceedings of the National Academy of Sciences of the USA, Jul. 2002.

Brightling, "Sputum induction in asthma", Chest 2006.

Domenico Spina, "Drugs for the treatment of respiratory diseases", Cambridge University Press, 2003.

ENDOBRONCHIAL FLUID EXHALER DEVICES AND METHODS FOR USE THEREOF

CROSS-REFERENCES TO RELATED APPLICATIONS

The present application claims the benefit of U.S. Provisional Patent Application 60/879,392 to Tolkowsky et al., filed Jan. 8, 2007, and U.S. Provisional Patent Application 60/906,200 to Tolkowsky et al., filed Mar. 12, 2007, which are both incorporated herein by reference.

FIELD OF THE INVENTION

The present invention generally relates to implanted medical apparatus. Specifically, the present invention relates to enhancing exhalation for subjects with Chronic Obstructive Pulmonary Disease (COPD).

BACKGROUND TO THE INVENTION

Chronic Obstructive Pulmonary Disease (COPD) is a group of lung diseases that afflict over 10 million Americans. These patients have been diagnosed with emphysema, chronic bronchitis, and/or asthma. Emphysema is characterized by the gradual, irreversible breakdown of lung tissue (i.e., destruction of structures supporting the alveoli and destruction of capillaries feeding the alveoli) and the subsequent loss of elasticity within the lungs. The breakdown of lung tissue dramatically reduces the ability of the lung to expel air, leading to an obstructive form of lung disease where airflow is impeded and air is generally "trapped" in the lungs.

Symptoms of emphysema include shortness of breath on exertion, typically when climbing stairs or inclines (and later at rest), hyperventilation and an expanded chest. As the disease advances, the damaged, inelastic areas of the lung progressively expand within the chest cavity, leaving the patient constantly feeling out of breath since there is insufficient room available for the lungs to function normally.

Traditionally, ameliorations for emphysema had included (i) medications, and (ii) highly-invasive Lung Volume Reduction (LVR) surgery where emphysematous regions are removed.

US Patent Application Publication 2005/0103340 to Wondka, which is incorporated herein by reference, describes methods, systems and devices for endobronchial ventilation using an endobronchially implanted ventilator for the purpose of treating COPD, emphysema and other lung diseases. Endobronchial drug delivery is also described using an endobronchially implanted drug pump, for therapeutic treatment of the lung or of other organs and tissues.

US Patent Application Publication 2003/0127090 to Gifford et al., which is incorporated herein by reference, describes a pump device that can be implanted into a body passageway, such as into a bronchial passageway. The pump device is described as being used to pump fluid through the body passageway, such as in order to assist the expiration of fluid from a region of the lung that fluidly communicates with the body passageway. The pump device includes a housing that defines an internal chamber, wherein fluid can flow through the chamber. The housing is dimensioned for insertion into a bronchial passageway. The pump device also includes a fluid propulsion mechanism in fluid communication with the chamber. The fluid propulsion mechanism is described as being positioned to propel fluid through the chamber so as to pump fluid through the bronchial passageway in a desired direction.

U.S. Pat. No. 6,679,264 to Deem et al., which is incorporated herein by reference, describes systems, methods and devices for performing pulmonary procedures, and in particular treating lung disease. A flow control element includes a valve that prevents airflow in the inhalation direction but permits airflow in the exhalation direction. The flow control element is guided to and positioned at the site by a bronchoscope that is introduced into the patient's trachea and used to view the lungs during delivery of the flow control element. The valve may include one, two or more valve elements, and it may be collapsible for easier delivery. A source of vacuum or suction may be used to increase the amount of fluid withdrawn from the lung tissue. A device for measuring hollow structures, such as bronchioles, and a device for removing a previously-placed flow control element are disclosed as well.

U.S. Pat. No. 6,258,100 to Alferness et al., which is incorporated herein by reference, describes a device, system, and method for lung size reduction by permanently collapsing at least a portion of a lung. The lung portion may be collapsed by obstructing the air passageway which communicates the lung portion to be collapsed. The air passageway may be obstructed by an obstructing member which precludes airflow in either direction or with a one-way valve which permits air to be exhaled from the lung portion while precluding air from being inhaled into the lung portion. In addition, a vacuum may be pulled within the lung portion to be collapsed for collapsing the lung portion and while the lung portion is collapsed the obstructing member may be placed in the air passageway to maintain the lung portion in a permanently collapsed state.

Boston Medical Products (MA), and Alveolus (NC) manufacture endobronchial stents for keeping obstructed airways open.

Broncus Technologies, Inc (CA) is investigating using the Exhale® Drug-Eluting Stent for an airway bypass procedure, described as a minimally-invasive treatment being studied to relieve emphysema symptoms. Airway bypass is described as creating new pathways in the lung for trapped air to escape and improving breathing mechanics, pulmonary function, and quality of life of people with emphysema.

The following patents and patent applications, which may be of interest, are incorporated herein by reference:
US Patent Application Publication 2004/0158294 to Thompson
U.S. Pat. No. 3,826,265 to Giori et al.
U.S. Pat. No. 5,611,335 to Makhoul et al.
US Patent Application Publication 2005/0025816 to Tanaka
US Patent Application Publication 2004/0237966 to Tanaka
US Patent Application Publication 2005/0015866 to Steinert
US Patent Application Publication 2006/0161233 to Barry et. al.
US Patent Application Publication 2006/0178552 to Gross
U.S. Pat. No. 5,972,026 to Laufer et al.
U.S. Pat. No. 6,283,988 to Laufer et al.
U.S. Pat. No. 6,694,979 to Deem et al.
U.S. Pat. No. 6,293,951 to Alferness et al.

SUMMARY OF THE INVENTION

In some embodiments of the invention, energy is extracted from a flow of air that is inhaled by a subject. The extracted energy is stored by a device inside an airway of the subject of the subject, and the energy is released when the subject exhales. Typically the energy is released in synchronization with a respiratory cycle of the subject, to assist exhalation of the subject. For some applications, energy is extracted by the rotation of a rotating member, e.g., a propeller, and energy is stored by winding a spring by the rotation of the rotating member. Energy is released by rotating the rotating member in an exhalation-assisting direction by unwinding the spring. Typically, the rotating member and the spring are placed in an airway of the subject, e.g., they are placed in one of the subject's bronchi.

In some embodiments, inhaled fluids are hindered from passing through the subject's airway distal to the device by placing a unidirectional valve within the airway.

In some embodiments, energy is alternatively or additionally extracted from motion of a portion of the subject's body.

In some embodiments of the invention, energy is extracted from movement of the subject's body, or a flow of fluid through the subject's body, over a period of time in which the body portion or the flow of fluid undergoes N cycles, N being an integer that is one or more, and typically, two or more. The extracted energy is stored and is subsequently released during N or fewer than N cycles. In some embodiments, the energy is extracted from the flow of fluid through the subject's body by rotating a propeller using the flow of fluid. For some applications, energy is extracted from the movement of the portion of the subject's body or the flow of fluid by using the movement or flow to store energy in a spring. In some embodiments, the energy is extracted from movement of a portion of the subject's body that moves in coordination with the respiratory cycle, for example, energy is extracted from motion of the diaphragm.

In some embodiments, energy is extracted from a flow of a fluid within a subject's body, and the energy is used to power a sensor that is implanted in the subject's body. For example, the flow of fluids may be used to rotate a propeller, and the energy extracted from the propeller is used to power a sensor. Typically, the sensor is electric and the propeller provides electrical power to the sensor via a generator. In some embodiments, energy is extracted from the flow of air through an airway of the subject, from the flow of blood through a blood vessel of the subject, and/or from the flow of urine through a urinary tract of the subject.

In some embodiments, a fluid exhaler is placed in a bronchial airway leading to functionally-impaired (e.g., emphysematous) lung regions. The fluid exhaler assists in conveying toward the trachea fluids trapped in the regions. The fluid exhaler, in certain embodiments, also hinders the entry of new fluids into the regions.

The fluid exhaler typically makes use of the naturally-induced flow of fluid in the lungs in the course of the respiratory cycle for at least two purposes. A first purpose is the generation of the exhaler's own powering, which typically reduces or eliminates the need for an added power supply such as an electrical battery. A second purpose is the synchronization of the exhaler's own action with the subject's respiratory cycle. For some applications, methods are provided for inserting the fluid exhaler through the airways, placing the exhaler at its designated location, activating the exhaler, and explanting the exhaler and removing it from the airways.

There is therefore provided in accordance with an embodiment of the invention, apparatus, including:

a first rotating member configured to be implanted in an airway of a subject and rotated in an inhalation direction by an inhaled flow of fluid in the airway; and a mechanical energy accumulator that is configured to accumulate energy from the rotation of the first rotating member.

In an embodiment, the first rotating member includes a propeller.

In an embodiment, the mechanical energy accumulator includes a spring that is configured to accumulate energy by being wound.

In an embodiment, the airway includes an airway in which inhaled fluid flows non-linearly, the inhalation direction is a direction that matches the non-linear flow of the inhaled fluid, and the rotating member is configured to rotate in the inhalation direction.

In an embodiment, the airway includes an anatomical portion selected from the group consisting of: a bronchus of the subject, an airway that leads to a lung of the subject, an airway that leads to a lobe of the subject, an airway that leads to a lobe segment of the subject, and an airway that leads to a lobule of the subject, and wherein the rotating member is configured to be implanted in the selected anatomical portion.

In an embodiment, the rotating member and the mechanical energy accumulator include non-magnetic materials that are configured to be placeable, while implanted within the subject, inside an MRI scanner.

In an embodiment, the apparatus further includes a material configured to dissolve secretions from the airway, and at least a portion of the apparatus is coated by the material.

In an embodiment, the apparatus further includes a friction-reducing material configured to reduce fluid friction, and at least a portion of the apparatus is coated by the friction-reducing material.

In an embodiment, the apparatus further includes a fibrosis-reducing material configured to reduce fibrosis of a wall of the airway, and at least a portion of the apparatus is coated by the fibrosis-reducing material.

In an embodiment, the apparatus further includes a cover, a portion of the apparatus is shaped to define an opening, and the cover is configured to reversibly cover the opening.

In an embodiment, the apparatus further includes an axis, the rotating member is mounted on the axis, the axis is shaped to define the opening, and the axis, by rotating in a first direction, is configured to uncover the opening.

In an embodiment, the axis, by rotating in a second direction opposite to the first direction, is configured to cover the opening.

In an embodiment, the axis is configured to uncover the opening in synchronization with a respiratory cycle of the subject.

In an embodiment, the apparatus further includes a placeholder configured to hold the rotating member and the mechanical energy accumulator within the airway.

In an embodiment, the placeholder includes a portion that is shaped as a spiral, and the spiraling of the portion of the placeholder is configured to affect a flow of fluid therethrough.

In an embodiment, the placeholder includes a portion that is shaped as a spiral, and the spiraling of the portion of the placeholder is configured to correspond to a non-linear flow of fluid therethrough.

In an embodiment, the placeholder includes arms, the arms being decouplable from the rotating member, the mechanical energy accumulator, and at least a portion of the placeholder.

In an embodiment, the placeholder includes a structure selected from the group consisting of: a tube structure, one or more springs, a mesh, a membrane, a stent, a cage, one or more rings, a grid, one or more rods configured to interface with the airway, one or more support arms configured to interface with the airway, and a sealing material.

In an embodiment, the apparatus further includes a unidirectional valve disposed at a distal end of the placeholder,
the unidirectional valve is configured to hinder inhaled fluids from passing through the distal end of the placeholder, and
the unidirectional valve is configured to allow exhaled fluids to pass therethrough.

In an embodiment, the unidirectional valve includes a valve selected from the group consisting of: a check valve, a leaf valve, a diaphragm-based valve, and a membrane-based valve.

In an embodiment, the unidirectional valve is configured to be closed during an inhalation phase of a respiratory cycle of the subject, and is configured to be open during an exhalation phase of the subject's respiratory cycle.

In an embodiment, the apparatus further includes an axis, the rotating member is mounted on the axis, and
the axis is configured to actuate synchronization of the opening of the unidirectional valve with the subject's respiratory cycle.

In an embodiment, the apparatus further includes an inner tunnel structure, disposed within the placeholder,
the rotating member and the mechanical energy accumulator are disposed within the inner tunnel structure, and
the inner tunnel structure is shaped to form an outer tunnel between the inner tunnel structure and the placeholder by being disposed within the placeholder.

In an embodiment, the unidirectional valve is configured to direct inhaled fluids proximally, via the outer tunnel.

In an embodiment, a distal portion of the inner tunnel structure is narrower than a proximal portion of the inner tunnel structure.

In an embodiment, a distal end of the inner tunnel structure curls away from a longitudinal axis of the inner tunnel structure.

In an embodiment, the placeholder is expansible.

In an embodiment, the placeholder is self-expansible.

In an embodiment, the apparatus further includes a grabbing feature, and the placeholder is configured to be expanded by applying a force to the grabbing feature.

In an embodiment, the grabbing feature includes a structure selected from the group consisting of: a ring, a loop, a switch, a push button, and a T lever.

In an embodiment, the apparatus further includes a grabbing feature, wherein the placeholder is configured to be contracted by applying a force to the grabbing feature.

In an embodiment, the grabbing feature includes a structure selected from the group consisting of: a ring, a loop, a switch, a push button, and a T lever.

In an embodiment, the mechanical energy accumulator includes a spring configured to be wound by extracting energy from motion of a portion of the subject's body in which the apparatus is disposed.

In an embodiment, the apparatus further includes a pendulum, and the spring is configured to extract energy from the motion of the portion of the subject's body via the pendulum.

In an embodiment, the spring is configured to be wound by motion of the airway of the subject.

In an embodiment, the mechanical energy accumulator includes a spring, and the spring is configured to assist exhalation of fluid from the airway by rotating the rotating member in an exhalation-assisting direction by the spring unwinding.

In an embodiment, the rotating member includes a propeller coupled to an axis, and the propeller is configured to wind the spring by rotating the axis.

In an embodiment, the apparatus further includes a gear coupled to the axis and configured to facilitate rotation of the axis during inhalation of the subject by a number of rotations that is not equal to one, per rotation of the propeller during inhalation of the subject.

In an embodiment, the apparatus further includes a gear coupled to the axis and configured to facilitate rotation of the axis in the exhalation-assisting direction by more than one rotation, per rotation of the axis in the inhalation direction.

In an embodiment, the propeller includes a bi-directional propeller configured to assist in an exhalation of a volume of fluid, per rotation of the propeller in the exhalation-assisting direction, that is approximately equal to an inhaled volume of fluid that rotates the propeller per rotation in the inhalation direction.

In an embodiment, the propeller includes a unidirectional propeller configured to assist in an exhalation of a volume of fluid, per rotation of the propeller in the exhalation-assisting direction, that is greater than an inhaled volume of fluid that rotates the propeller per rotation in the inhalation direction.

In an embodiment, the mechanical energy accumulator is configured to assist exhalation of fluid from the airway during an exhalation phase of a respiratory cycle of the subject.

In an embodiment, the mechanical energy accumulator is configured not to assist exhalation of fluid from the airway during an inhalation phase of a respiratory cycle of the subject.

In an embodiment, the mechanical energy accumulator includes a spring that is configured to accumulate energy by being wound during N inhalations of the subject, and wherein the spring is configured to release energy by unwinding during fewer than N exhalations of the subject.

In an embodiment, the apparatus further includes a device selected from the group consisting of a ratchet and a gear, wherein the selected device is configured to facilitate the energy accumulation of the spring.

In an embodiment, the apparatus further includes a sensor configured to detect a phase of a respiratory cycle of the subject, and the mechanical energy accumulator is configured to release energy in response to the detected phase.

In an embodiment, the sensor includes a motion sensor configured to detect motion of a diaphragm of the subject.

In an embodiment, the sensor includes a chemical sensor configured to detect a chemical composition within an airway of the subject.

In an embodiment, the apparatus further includes a motor configured to rotate the rotating member in the exhalation-assisting direction.

In an embodiment, the apparatus further includes an implantable battery that is configured to power the motor.

In an embodiment, the apparatus further includes a battery configured to be disposed outside the subject's body and configured to wirelessly power the motor.

In an embodiment, the rotating member includes a first propeller and a second propeller disposed concentrically to the first propeller, the second propeller having airfoils that are disposed in a different direction from airfoils of the first propeller, and the second propeller being configured to be rotated by unwinding of the mechanical energy accumulator.

In an embodiment, the apparatus further includes an axis, wherein the first and second propellers are mounted on the axis, the first propeller is configured to wind the mechanical energy accumulator by rotating the axis in the inhalation direction during an inhalation phase of a respiratory cycle of the subject, and the mechanical energy accumulator is configured to rotate the second propeller in an exhalation-assisting direction, by rotating the axis during an exhalation phase of the subject's respiratory cycle.

In an embodiment, the apparatus further includes a clutch, coupled to the axis and configured to facilitate synchronization of the rotations of the propellers with the respiratory cycle of the subject.

There is additionally provided, in accordance with an embodiment of the invention, apparatus for use with a portion of a subject's body that undergoes cyclical motion, the apparatus including:

an energy accumulator configured to store energy from movement of the subject's body over a period of time in which the body portion undergoes N cycles, N being two or more; and an energy release mechanism configured to release the stored energy during fewer than N cycles.

In an embodiment, the energy accumulator is configured not to accumulate energy at the same time as the energy release mechanism releases energy.

In an embodiment, the energy accumulator is configured to accumulate energy at the same time as the energy release mechanism releases energy.

In an embodiment, the energy accumulator includes a rotating member configured to be rotated by a flow of fluid through the subject's body.

In an embodiment, the rotating member is configured to be placed in an airway of the subject and is configured to accumulate energy from the flow of fluid through the airway.

In an embodiment, the rotating member is configured to be placed in a blood vessel of the subject and is configured to accumulate energy from the flow of blood through the blood vessel.

In an embodiment, the energy accumulator includes a spring configured to accumulate energy by being contracted by movement of a portion of the subject's body.

In an embodiment, the spring is configured to be placed in a vicinity of a heart of the subject and is configured to be contracted by movement of the subject's heart.

In an embodiment, the spring is configured to be placed inside a heart of the subject and is configured to be contracted by movement of the subject's heart.

In an embodiment, the spring is configured to be placed in a vicinity of a blood vessel selected from the group consisting of: a blood vessel of the heart of the subject, an aorta of the subject and a vena cava of the subject.

In an embodiment, the spring is configured to be placed in a vicinity of a blood vessel of the subject and is configured to be contracted by movement of the subject's blood vessel.

In an embodiment, the spring is configured to be placed inside a blood vessel of the subject and is configured to be contracted by movement of the subject's blood vessel.

There is still additionally provided, in accordance with an embodiment of the invention, apparatus including:

a sensor configured to be implanted in a subject's body; and an energy extractor configured to extract energy from a flow of a fluid within the subject's body and to power the sensor using the extracted energy.

In an embodiment, the energy extractor includes a rotating member configured to extract energy from the flow of fluid through the subject's body.

In an embodiment, the rotating member is configured to be placed in an airway of the subject and is configured to extract energy from a flow of fluid through the airway.

In an embodiment, the rotating member is configured to be placed in a blood vessel of the subject and is configured to extract energy from the flow of blood through the blood vessel.

In an embodiment, the rotating member is configured to be placed in a urinary tract of the subject and is configured to extract energy from the flow of urine through the urinary tract.

There is still additionally provided, in accordance with an embodiment of the invention, a method, including:

extracting energy from a flow of fluid that is inhaled by a subject;

storing the extracted energy in an airway of the subject; and releasing the energy when the subject exhales.

In an embodiment, extracting energy includes extracting energy during N inhalations of the subject, and releasing energy includes releasing energy during fewer than N exhalations of the subject.

In an embodiment, releasing the energy includes assisting exhalation of the subject in synchronization with a respiratory cycle of the subject.

In an embodiment, extracting energy includes rotating a rotating member.

In an embodiment, storing the extracted energy in an airway of the subject of the subject includes storing the extracted energy in a location selected from the group consisting of: a bronchus of the subject, an airway that leads to a lobe of the subject, an airway that leads to a lobe segment of the subject, and an airway that leads to a lobule of the subject.

In an embodiment, the method further includes dissolving secretions of an airway of the subject.

In an embodiment, extracting energy includes rotating a propeller that is mounted on an axis.

In an embodiment, the method further includes uncovering an opening in the axis by rotating the propeller.

In an embodiment, uncovering the opening includes uncovering the opening in synchronization with a respiratory cycle of the subject.

In an embodiment, the method further includes administering medication to the subject via the opening.

In an embodiment, the method further includes inserting a probe into an airway of the subject via the opening.

In an embodiment, the flow of fluid includes a flow of fluid in an airway of the subject, and the method further includes hindering inhaled fluids from passing through the subject's airway by placing a unidirectional valve within the airway.

In an embodiment, the method further includes opening the unidirectional valve in synchronization with a respiratory cycle of the subject.

In an embodiment, the method further includes directing inhaled fluid in a proximal direction.

In an embodiment, the method further includes inserting an energy extractor into an airway of the subject, the energy extractor being configured to extract the energy from the inhaled flow of fluid.

In an embodiment, the method further includes producing an image of the airway, and inserting the energy extractor includes navigating the energy extractor using the produced image.

In an embodiment, the method further includes inserting a bronchoscope into the airway and removing the bronchoscope, wherein inserting the energy extractor includes inserting the energy extractor subsequent to the bronchoscope having been removed.

In an embodiment,
the energy extractor includes at least an expansible portion, and
inserting the energy extractor includes:
inserting an expansible structure into the airway,
expanding the expansible structure,
inserting the expansible energy extractor into the airway, and coupling the energy extractor to the expansible structure by expanding the expansible portion of the energy extractor.

In an embodiment, inserting the energy extractor includes expanding an expansible structure that is coupled to the energy extractor while the energy extractor is within the airway.

In an embodiment, the method further includes contracting the expansible structure and removing the expansible structure and the energy extractor from the airway subsequent to the contracting.

In an embodiment, the method further includes inserting a bronchoscope into the airway, inserting the energy extractor includes inserting the energy extractor via the bronchoscope, and expanding the structure includes expanding the structure while the bronchoscope is within the airway.

In an embodiment, the method further includes inserting a probe into the airway, inserting the energy extractor includes inserting the energy extractor via the probe, and expanding the structure includes expanding the structure while the probe is within the airway.

In an embodiment, inserting the energy extractor includes:
inserting an expansible structure into the airway,
expanding the expansible structure,
inserting the energy extractor into the airway, and
coupling the energy extractor to the expansible structure.
In an embodiment, the method further includes:
decoupling the energy extractor from the expansible structure,
removing the energy extractor from the airway, and
leaving at least a portion of the expansible structure within the airway for more than one month.

In an embodiment, the method further includes extracting energy from motion of a portion of the subject's body.

In an embodiment, the flow of fluid includes a flow of fluid in an airway of the subject, and extracting energy from motion of the portion includes winding a spring using motion of the airway.

In an embodiment, storing the extracted energy includes winding a spring, and releasing the stored energy includes unwinding the spring.

In an embodiment, extracting the energy includes rotating a first propeller in an inhalation direction, the rotation of the propeller being configured to wind the spring.

In an embodiment, releasing the energy includes assisting exhalation of the subject by rotating a second propeller in an exhalation-assisting direction by unwinding the spring, the second propeller being disposed concentrically to the first propeller, and the second propeller having airfoils that are disposed in a different directions to airfoils of the first propeller.

In an embodiment, releasing the energy includes assisting exhalation of the subject by rotating the propeller in an exhalation-assisting direction by unwinding the spring.

In an embodiment, the method further includes assisting exhalation of the subject by rotating the propeller in an exhalation-assisting direction using a motor.

In an embodiment, rotating the propeller in the exhalation-assisting direction includes rotating the propeller in the exhalation-assisting direction by more than one rotation per rotation of the propeller in the inhalation direction.

In an embodiment, rotating the propeller in the exhalation-assisting direction, includes facilitating an exhalation of a volume of fluid, per rotation, that is approximately equal to an inhaled volume of fluid that rotates the propeller per rotation in the inhalation direction.

In an embodiment, rotating the propeller in the exhalation-assisting direction includes facilitating an exhalation of a volume of fluid, per rotation, that is greater than an inhaled volume of fluid that rotates the propeller per rotation in the inhalation direction.

In an embodiment, the method further includes detecting a phase of a respiratory cycle of the subject, extracting energy includes extracting energy in synchronization with the respiratory cycle, and releasing energy includes releasing energy in synchronization with the respiratory cycle.

In an embodiment, detecting the phase includes detecting motion of a diaphragm of the subject.

In an embodiment, detecting the phase includes detecting a chemical composition within an airway of the subject.

In an embodiment, flow of fluid includes a non-linear flow of fluid, and extracting energy includes extracting energy from the non-linearity of the flow of fluid.

In an embodiment, the method further includes examining the subject to determine a direction of the non-linear flow and choosing an energy extractor for extracting energy from the flow of fluid and for inserting into an airway of the subject in response to the determining.

There is still additionally provided, in accordance with an embodiment of the invention, a method for use with a portion of a subject's body that undergoes cyclical motion, the method including:
extracting energy from movement of the subject's body over a period of time in which the body portion undergoes N cycles, N being two or more;
storing the extracted energy; and
releasing the energy during fewer than N cycles.
In an embodiment, extracting energy includes not extracting energy during cycles in which energy is released.

In an embodiment, extracting energy includes extracting energy during cycles in which energy is released.

In an embodiment, extracting energy includes extracting energy from a flow of fluid through the subject's body.

In an embodiment, extracting energy includes rotating a rotating member.

In an embodiment, extracting energy includes extracting energy from a flow of fluid through an airway of the subject.

In an embodiment, extracting energy includes extracting energy from a flow of blood through a blood vessel of the subject.

In an embodiment, extracting energy includes extracting energy from movement of a portion of the subject's body.

In an embodiment, extracting energy includes contracting a spring.

In an embodiment, extracting energy includes extracting energy from movement of a heart of the subject.

In an embodiment, extracting energy includes extracting energy from movement of a blood vessel of the subject.

There is still additionally provided, in accordance with an embodiment of the invention, a method including:
extracting energy from a flow of a fluid within a subject's body; and
powering a sensor that is implanted in the subject's body using the extracted energy.
In an embodiment, extracting energy includes extracting energy by rotating a rotating member.

In an embodiment, extracting energy includes extracting energy from a flow of fluid through an airway of the subject.

In an embodiment, extracting energy includes extracting energy from a flow of blood through a blood vessel of the subject.

In an embodiment, extracting energy includes extracting energy from a flow of urine through a urinary tract of the subject.

The present invention will be more fully understood from the following detailed description of embodiments thereof, taken together with the drawings, in which:

DETAILED DESCRIPTION OF EMBODIMENTS

Figure 1A:
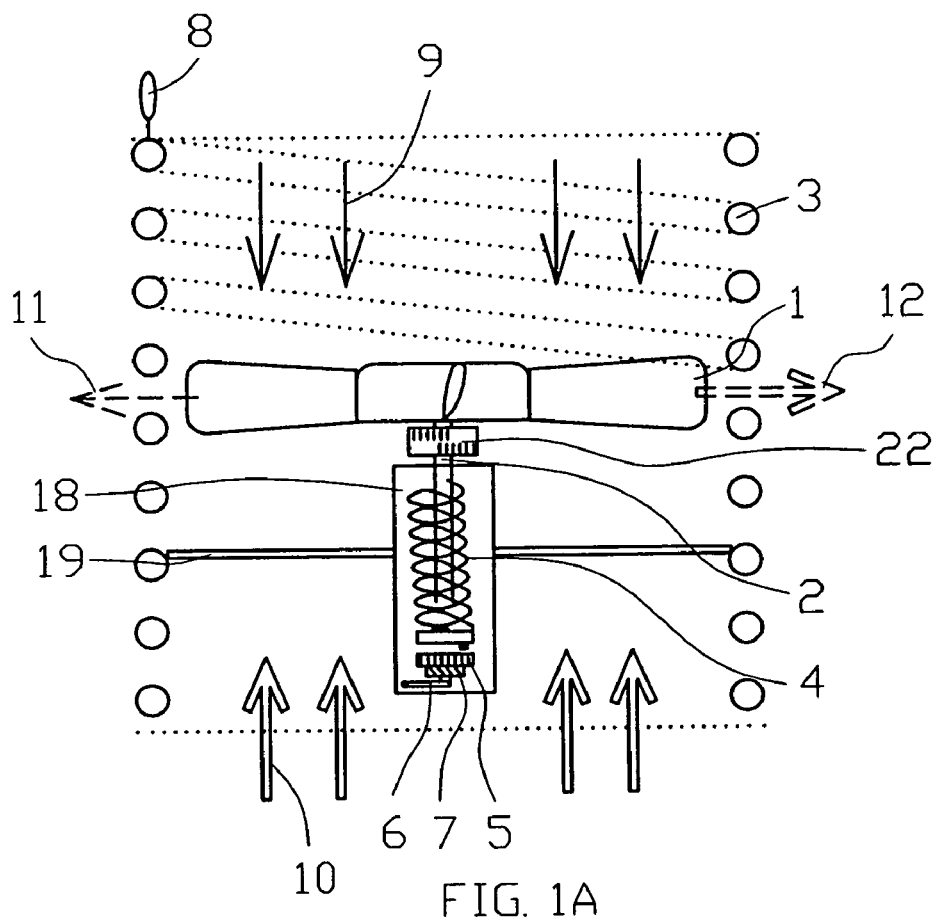
FIGS. 1A-C are schematic illustrations of an endobronchial fluid exhaler, in accordance with a first embodiment of the present invention.

In some embodiments of the invention, devices and methods for use thereof improve the quality of life of patients living with Chronic Obstructive Pulmonary Disease (COPD) in general, and in particular those patients with lung emphysema. The devices improve the flow of fluid in such patients' airways, and typically comprise a fluid exhaler that is placed in a bronchial airway leading to a functionally-impaired (e.g., emphysematous) distal lung region. Typically, the fluid exhaler assists in conveying toward the trachea fluids trapped in the distal region. In some embodiments, the fluid exhaler also hinders the entry of new fluids into the distal region.

As used herein:

The term "fluid" means a gas, a liquid, and/or combinations of gas(es) and liquid(s). Normally, such fluids flowing in the airways are mostly gases, however they may also comprise liquids such as secretions.

The terms "proximal" and "proximally" mean toward the trachea, and the terms "distal" and "distally" mean away from the trachea. However when referring to a position inside the trachea, the terms "proximal" and "proximally" mean toward the mouth, and the terms "distal" and "distally" mean away from the mouth.

The terms "active" and "actively" mean making use of energy provided by some form of an energy accumulator and/or energy transmitter.

In some embodiments of the invention, a fluid exhaler makes use of the naturally-induced flow of fluid in the lungs in the course of the respiratory cycle for the generation of its own power and for the inherent synchronization of its own action with the subject's respiratory cycle.

For its own power, the exhaler typically comprises a powering mechanism in the form of an energy accumulator and releaser. In an embodiment, the energy accumulator and releaser comprise a winding spring that is coupled via an axis of rotation to one or more propellers. The winding spring is wound by inhaled fluids interacting with the propellers during an inhalation phase of the respiratory cycle. Specifically, inhaled fluids cause the rotation of the propeller(s), which causes the rotation of the axis of rotation, which causes the winding of the spring.

When inhalation of fluids ceases, the spring ceases to be wound. After one winding or after a determined number of windings (wherein such number may be set by a counter mechanism such as a ratchet), the spring unwinds. By unwinding, the spring causes, via the aforementioned axis and propeller(s), the exhalation of fluids during the exhalation phase of the respiratory cycle.

In other words, the naturally-induced flow of fluids during the respiratory cycle is typically used not only for the accumulation of energy to assist in exhalation of fluids, but also for the timely release of such energy in a manner that is synchronized with the subject's natural respiration. The unwinding of the spring, causing the rotation of the axis and propellers and consequent release of energy, occurs during the exhalation phase of a respiratory cycle (but not necessarily of every respiratory cycle).

Typically, the force applied by the exhaler to exhale fluid is such that it reduces the likelihood of the endobronchial walls collapsing and trapping air in the distal lung section once the exhaler is activated. Typically, the exhalation force is less than or equal to the force naturally applied by the respiratory system to achieve normal exhalation in healthy patients, e.g., between 30% and 70% or between 70% and 100% of the exhalation force that is typically produced naturally by a healthy subject. Alternatively, the force is below or above these ranges.

In some embodiments, additional techniques for synchronization of the exhaler with the natural respiratory cycle comprise sensing the movement of the subject's chest walls, or sensing the composition (e.g., oxygen, $CO_2$) of fluid in the airways, or any combination thereof.

For some applications, an additional naturally-induced source of energy for energy accumulation into the aforementioned winding spring is the natural motion of the fluid exhaler device as a whole, wherein such motion may also occur together with the bronchial lumen in which it is implanted. An article by Berbeco et al., entitled "Residual motion of lung tumors in gated radiotherapy with external respiratory surrogates," Phys Med Biol. 2005 Aug. 21; 50 (16):3655-67, and an article by Stock et al., entitled "Development and application of a real-time monitoring and feedback system for deep inspiration breath hold based on external marker tracking," Med Phys. 2006 August; 33 (8):2868-77, which are both incorporated herein by reference, teach that lung masses move by as much as 3 cm during the respiratory cycle. While that was specifically investigated on biological lung masses such as tumors, it generally applies to any mass within the lungs including an implanted endobronchial device. In some embodiments, the motion of such mass during the respiratory cycle, which typically occurs several thousands (or more) of times per day, is in turn also used to wind the spring.

In some embodiments, the winding is achieved using the principles through which a self-winding watch operates. For example, motion may be converted into winding a spring via a transmission that also comprises a weight, a pendulum, a train gear or any combination thereof.

In some embodiments, the motion used to cause the winding of the spring alternatively or additionally comprises expansion or contraction of the endobronchial lumen against the exhaler during the respiratory cycle, or any other motion of the subject's body.

Other embodiments of an energy accumulator comprise a fluid chamber which is compressed to accumulate energy and subsequently expanded to release energy.

In some embodiments, the rotation of the propeller(s) is caused or assisted by a motor whose energy supply comprises an electric battery situated within a bronchial airway, an electric battery situated outside the bronchial airways but within the subject's body, an electric battery situated outside the subject's body (including a disposable battery such as a patch on the subject's skin), and/or a capacitor accumulating and releasing energy, or any combination thereof. For example, connection of the energy supply to the motor may be wired or wireless or a combination thereof, with one or more antennas used in the case of a wireless connection. For some applications, in the above-described case of a battery patch, the antenna(s) may be embedded within the battery patch.

In some embodiments, energy for the motor is transmitted from outside the subject's body. For some applications, the energy comprises energy transmitted via radiofrequency, energy transmitted via ultrasound, energy transmitted via a magnetic field, energy transmitted via an electromagnetic field, or any combination thereof among themselves and together with any of the previously-described sources of energy. Transmission of energy from outside the subject's body typically comprises the use of one or several antenna(s).

In an embodiment, the fluid exhaler is constructed from MRI-compatible materials, so that its presence in the body of a subject does not exclude the subject from being imaged by MRI.

In an embodiment, components of the exhaler interacting with fluid are coated with a material (such as an enzyme) that typically dissolves endobronchial secretions. In such a case, any potential degrading effect of such secretions on the operation of the exhaler is typically mitigated.

In an embodiment, components of the exhaler interacting with fluid are coated with a smooth material (such as Teflon or silicon), such that loss of energy due to friction is typically reduced. In an embodiment, such a coating is applied to one side of the blades of the propeller(s), such as the distal side or the proximal side, but not to the other side.

In an embodiment, components of the exhaler interacting with the endobronchial wall are covered with a material (such as Teflon) that typically assists in avoiding or reducing the formation over time of granulation tissue and fibrosis.

In an embodiment, the endobronchial exhaler comes in a selection of diameters suitable for placement in a variety of bronchial lumens.

In an embodiment, the endobronchial fluid exhaler is applied to treating types of Chronic Obstructive Pulmonary Disease (COPD) besides emphysema, such as asthma or bronchitis.

The figures of the present patent application show four different embodiments of the endobronchial fluid exhaler. For each figure n having a suffix A, B, or C, Fig. n(A) shows a side section, Fig. n(B) shows a cross section, and Fig. n(C) shows placement of a device within a bronchial airway.

In all figures, arrows are used to indicate directions in the following manner:

Arrows with single solid lines indicate the flow of fluid that is inhaled in the inhalation phase of the respiratory cycle.

Arrows with double solid lines indicate the flow of fluid that is exhaled in the exhalation phase of the respiratory cycle.

Arrows with single dashed lines indicate the rotation of a propeller in a direction corresponding to the inhalation of fluids.

Arrows with double dashed lines indicate the rotation of a propeller in a direction corresponding to the exhalation of fluids.

Figure 1B:
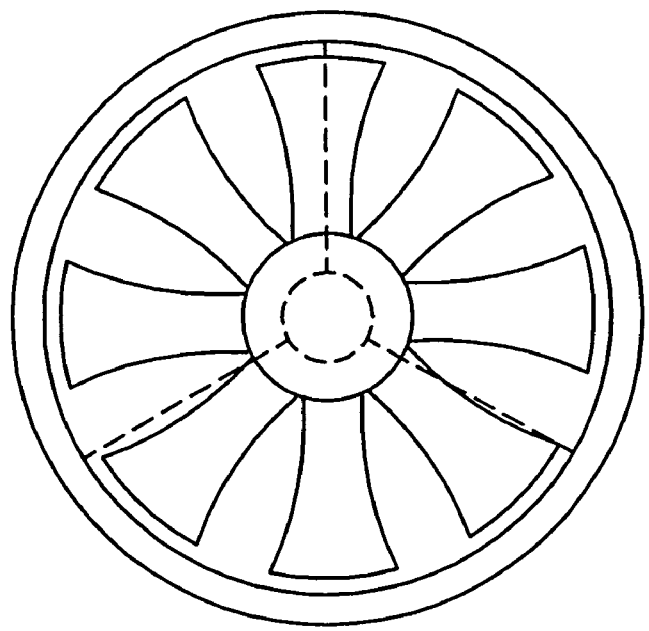
Figure 1C:
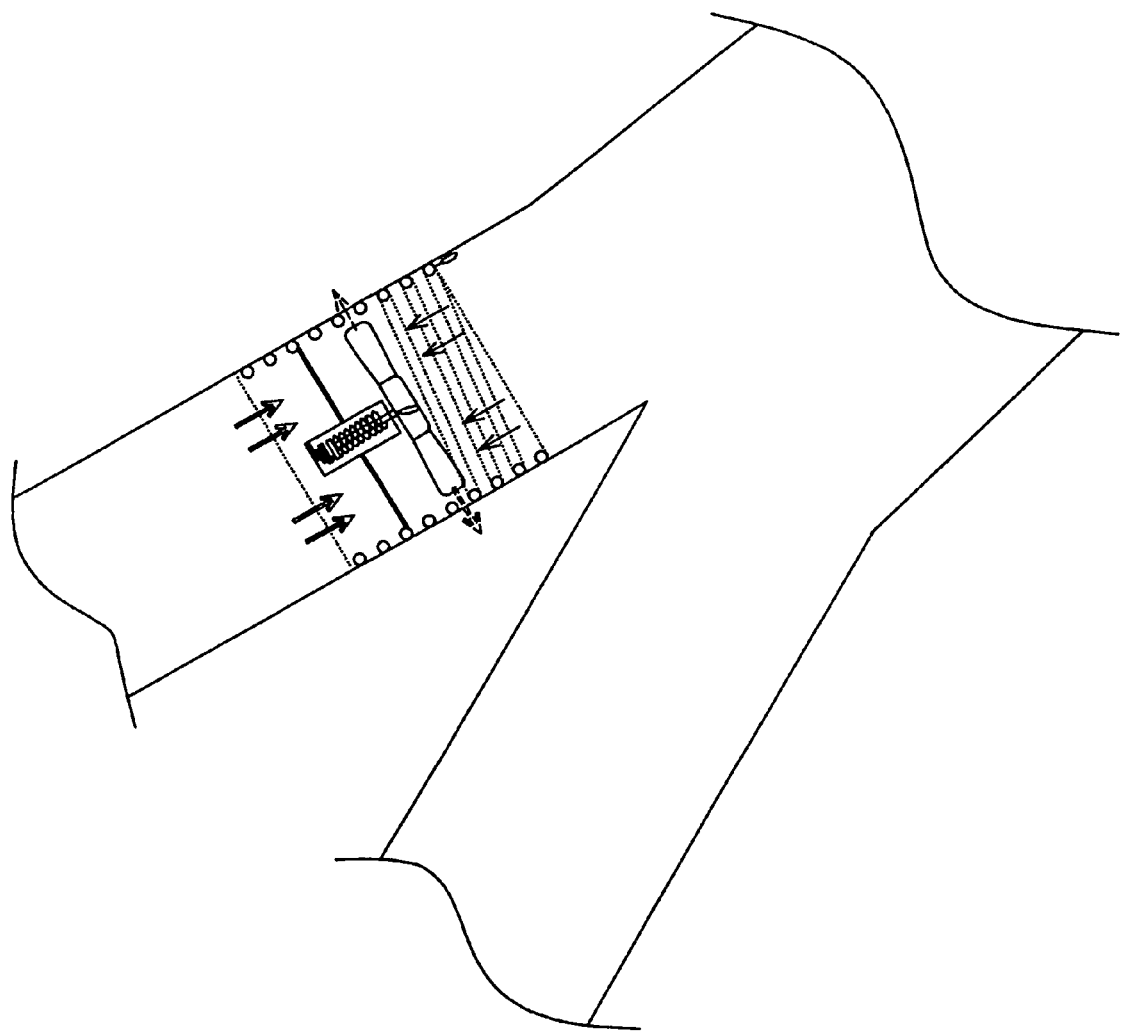

Reference is now made to FIGS. 1A, 1B and 1C, which are schematic illustrations of a first embodiment of an endobronchial fluid exhaler which typically comprises one or more axial propellers 1 that interact with the fluids, an axis of rotation 2 on which each such propeller(s) is mounted, and a placeholder 3 for keeping the axis and propeller(s) positioned against the endobronchial lumen. In some embodiments, the placeholder is expandable and contractible. In some embodiments the placeholder is self-expanding. Typically, the exhaler includes arms 19 that connect placeholder 3 to axis 2, and/or to a housing 18 within which axis 2 resides.

In some embodiments, placeholder 3 comprises a tube-like structure, a sleeve-like structure, one or more springs, a mesh, a tubular structure, a membrane, a stent, a cage, one or more rings, a grid, one or more rods interfacing with the endobronchial wall, one or more support arms interfacing with the endobronchial wall, or any combination thereof. Alternatively or additionally, the placeholder comprises a sealing to facilitate its attachment to the endobronchial lumen.

In some embodiments, the cross section of the blades of propeller(s) 1 (also known as the airfoil of the propeller) is such that the propeller typically interacts at a similarly-high efficiency with the flow of inhaled fluid 9 while rotating in direction 11 and with the flow of exhaled fluid 10 while rotating in the opposite direction 12. Such a propeller is termed bi-directional.

In alternative embodiments, the airfoil of the blades of propeller(s) 1 is unidirectional in the sense that interaction with the flow inhaled fluid 9 while rotating in direction 11 typically differs in its efficiency from interaction with the flow of exhaled fluid 10 while rotating in the opposite direction 12.

In some embodiments, a main spring 4 interacts with axis 2. Main spring 4 is typically wound by fluid 9 passing in the distal direction through propeller(s) 1 during the inhalation phases of the respiratory cycle. The fluid typically causes the rotation of propeller(s) 1 in the inhalation direction 11, which in turn causes the rotation of axis 2, which in turn causes the winding of main spring 4. Subsequently, once the inhalation phase of the respiratory cycle concludes and the exhalation phase begins, the energy accumulated in main spring 4 is released in the form of main spring 4 unwinding. Such unwinding causes the rotation of axis 2 in exhalation direction 12, which causes the rotation of propeller(s) 1 in exhalation direction 12, which facilitates the exhalation of fluid 10 from the lung segment that is distal to the exhaler and toward the trachea.

In an embodiment, a gear 22 is connected to axis 2. The gear enables the transmission ratio between the rotation of axis 2 and the rotation of propeller(s) 1 to be different from 1:1.

For some applications, propeller(s) 1 wind spring 4 when rotating in the inhalation direction 11, and the propellers are assisted by unwinding of the spring during exhalation. There is thus greater resistance to rotation of the propeller(s) during inhalation than during exhalation. In some embodiments, the difference in the resistance between rotation during inhalation versus rotation during exhalation enables the exhaler to transfer more fluid from its distal side to its proximal side during exhalation than it transfers from its proximal side to its distal side during inhalation. Thus, over time, the amount of fluid that is trapped in an emphysematous region that is distal to the exhaler is reduced, or eliminated.

Other embodiments for creating or increasing the aforementioned difference between resistance to rotation of the propeller(s) in the inhalation direction versus resistance to the rotation of the propeller(s) in the exhalation direction, and thus the ability of the exhaler to transfer more fluid from its distal side to its proximal side during exhalation than it does from its proximal side to its distal side during inhalation, include: applying different smoothness to the two sides of the blades of propeller(s) 1; constructing propeller(s) 1 with a unidirectional airfoil; implementing optional gear 22 with a transmission ratio such that a single rotation of axis 2 in inhalation direction 11 corresponds to multiple rotations of axis 2 in exhalation direction 12; or any combination thereof.

In an embodiment, an inner surface of placeholder 3 or a spring placed therein spirals (proximal to distal) in direction 11, so that its directionality affects the flow of fluid and further enhances the efficacy of the exhaler.

Typically, main spring 4 is made of a material that is structurally strong and also has a memory shape, such that it is particularly suitable for a very large number of windings and unwindings.

In an embodiment, main spring 4 accumulates energy, with the help of an optional counter mechanism 5, during the inhalation phase of multiple respiratory cycles before it unwinds to assist exhalation of fluids during the exhalation phase of one or several respiratory cycles. In such a case, a greater amount of energy unwinds main spring 4 which causes a greater exhalation of fluids 10 by propeller(s) 1 once it rotates in the exhalation direction 12. Furthermore, such an arrangement is typically useful when the amount of energy accumulated in main spring 4 during a single inhalation is relatively small. For example, counter mechanism 5 may be implemented in the form of a mechanical counter such as a ratchet or a gear.

In an embodiment, housing 18 isolates axis 2 and main spring 4, fully or partially, from endobronchial secretions whose accumulation might degrade the ability of spring 4 to wind and unwind.

Making use of naturally-induced inhalation of fluids during the respiratory cycle typically has at least two purposes. One purpose is the accumulation of energy into main spring 4 as described above. A second purpose is the synchronization of the direction of rotation of propellers(s) 1 with the subject's natural respiratory cycle. Specifically, in some embodiments, the above-described mechanism causes propeller(s) 1 to rotate in the direction of exhalation 12 during an exhalation phase of a respiratory cycle, but generally not during an inhalation phase of a respiratory cycle.

In some embodiments, an additional naturally-induced source of energy for winding main spring 4 is the natural motion of the fluid exhaler device as a whole during the respiratory cycle. The motion is converted into further winding of main spring 4 via an energy conversion mechanism. In some embodiments, the energy conversion mechanism comprises one or more pendulums 6, operating in one or more planes to accommodate different body positions, and a transmission 7.

In some embodiments, the motion used to cause the winding of main spring 4 comprises the expansion and contraction of the endobronchial lumen against placeholder 3 during the respiratory cycle, and/or any other motion of the subject's body.

In some embodiments, sources of energy for the rotation of axis 2 during an exhalation phase of the respiratory cycle may also comprise any of the other forms of energy accumulation, transmission and release that are described herein.

In some embodiments, a grabbing feature 8 is situated at the fluid exhaler's proximal side. Embodiments of the feature include a ring, a loop, a switch, a push button, a T-like lever, or any combination thereof. Applying force to grabbing feature 8, for example by interacting with the feature with a standard endoscopic tool such as biopsy forceps, causes the fluid exhaler in its entirety or placeholder 3 in particular to expand. The expansion is used for fixing the fluid exhaler's position against the endobronchial lumen during implantation. Conversely, applying another force on grabbing feature 8 (or on another grabbing feature) causes either the fluid exhaler in its entirety, or placeholder 3 in particular, to contract with respect to the endobronchial lumen during explanation, so that it may be separated from the luminal tissue and removed.

The ability to expand and contract the exhaler as a whole is frequently useful when inserting or removing the exhaler through a working channel of a bronchoscope, as explained hereinbelow.

In an embodiment, arms 19 are detachable such that most components of the exhaler can be removed from the subject's body while placeholder 3 remains in place. This feature is frequently useful when the exhaler is removed after having been implanted for some period, during which placeholder 3 has already become attached to or within the tissue of the endobronchial wall. Another case where this feature is useful is in embodiments in which placeholder 3 is inserted and placed in the endobronchial lumen in a separate step from the placement of the rest of the exhaler, as described hereinbelow.

In an embodiment, the exhaler or parts thereof are manufactured by a process of etching, including (but not limited to) laser etching. In an embodiment, the exhaler or parts thereof are manufactured by a process of stereo-lithography.

In an embodiment, arms 19 are both attachable and detachable.

Reference is now made to FIGS. 2A-C which are schematic illustrations of an endobronchial fluid exhaler that includes (a) a unidirectional valve 14 at its distal section, and (b) an inner tunnel 13, in accordance with a second embodiment of the present invention. In all other aspects, this second exhaler is generally similar to the first exhaler disclosed in FIGS. 1A, 1B and 1C. Therefore, embodiments of the invention that are described with respect to the first exhaler that also apply to the second exhaler are generally not repeated herein.

In some embodiments, the additions of inner tunnel 13 and unidirectional valve(s) 14 enables the second exhaler to further hinder, or prevent, inhaled fluid 9 from entering (from the direction of the exhaler) the lung segment that is distal to the exhaler.

Propeller(s) 1 typically has a smaller diameter than inner tunnel 13. Propeller(s) 1 is typically situated within inner tunnel 13. For some applications, inner tunnel 13 is narrower in its distal section compared with its proximal section. In some embodiments, the distal section of inner tunnel 13 has a curled form.

In some embodiments, unidirectional valve(s) 14 comprises a check valve of any type (e.g., ball check, duckbill, swing check, clapper, stop check), a leaf valve, a diaphragm, a membrane, or any combination thereof, or any other suitable valve.

Inhaled fluid 9 flows through inner tunnel 13 while rotating propeller(s) 1 in direction 11. The rotation of propeller(s) 1 causes the rotation of axis 2 in the inhalation direction 11, which causes the winding of main spring 4. In addition, distal unidirectional valves(s) 14 prevents or hinders the inhaled fluids from further entering the lung area distal to the fluid exhaler. Instead, inhaled fluids flow back toward the trachea through the space between inner tunnel 13 and placeholder 3 with the space embodying an outer tunnel.

During an exhalation phase of the respiratory cycle, main spring 4 unwinds, which causes the rotation of axis 2 in the exhalation direction 12, which causes propeller(s) 1 to rotate in the exhalation direction 12 and exhale fluid 10 back from the lung segment distal to the exhaler and toward the trachea. The exhaled fluid 10 passes in the direction of exhalation through unidirectional valve(s) 14 and inner tunnel 13.

In an embodiment, unidirectional valve(s) 14 comprise a mechanism that is synchronized with the respiratory cycle, such that they open during the exhalation phase and close (fully or partially) during the inhalation phase, to increase the efficacy of the exhaler. For example, such synchronization may be implemented by axis 2 extending to valve(s) 14 and serving by means of its rotation (in direction 11 during inhalation and in direction 12 during exhalation) as an actuator for the opening and closing of the valve.

In an embodiment, the opening of valve(s) 14 is synchronized with the respiratory cycle and the exhaler does not necessarily include inner tunnel 13.

Figure 3A:
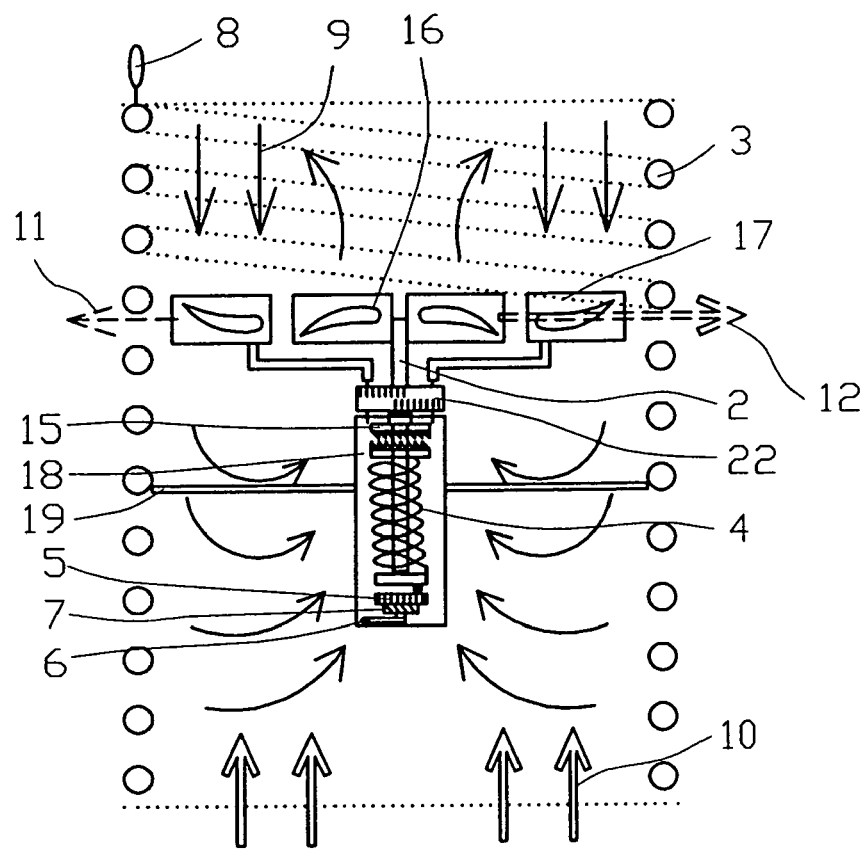
FIGS. 3A-C are schematic illustrations of an endobronchial fluid exhaler that includes two separate but concentric propellers, in accordance with a third embodiment of the present invention.
Figure 3B:
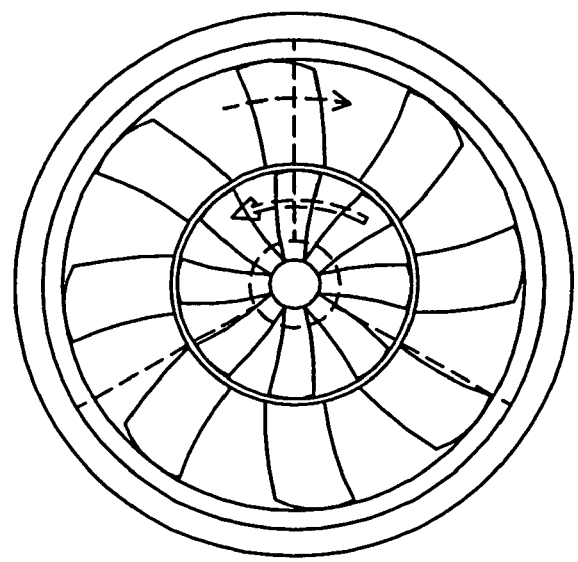
Figure 3C:
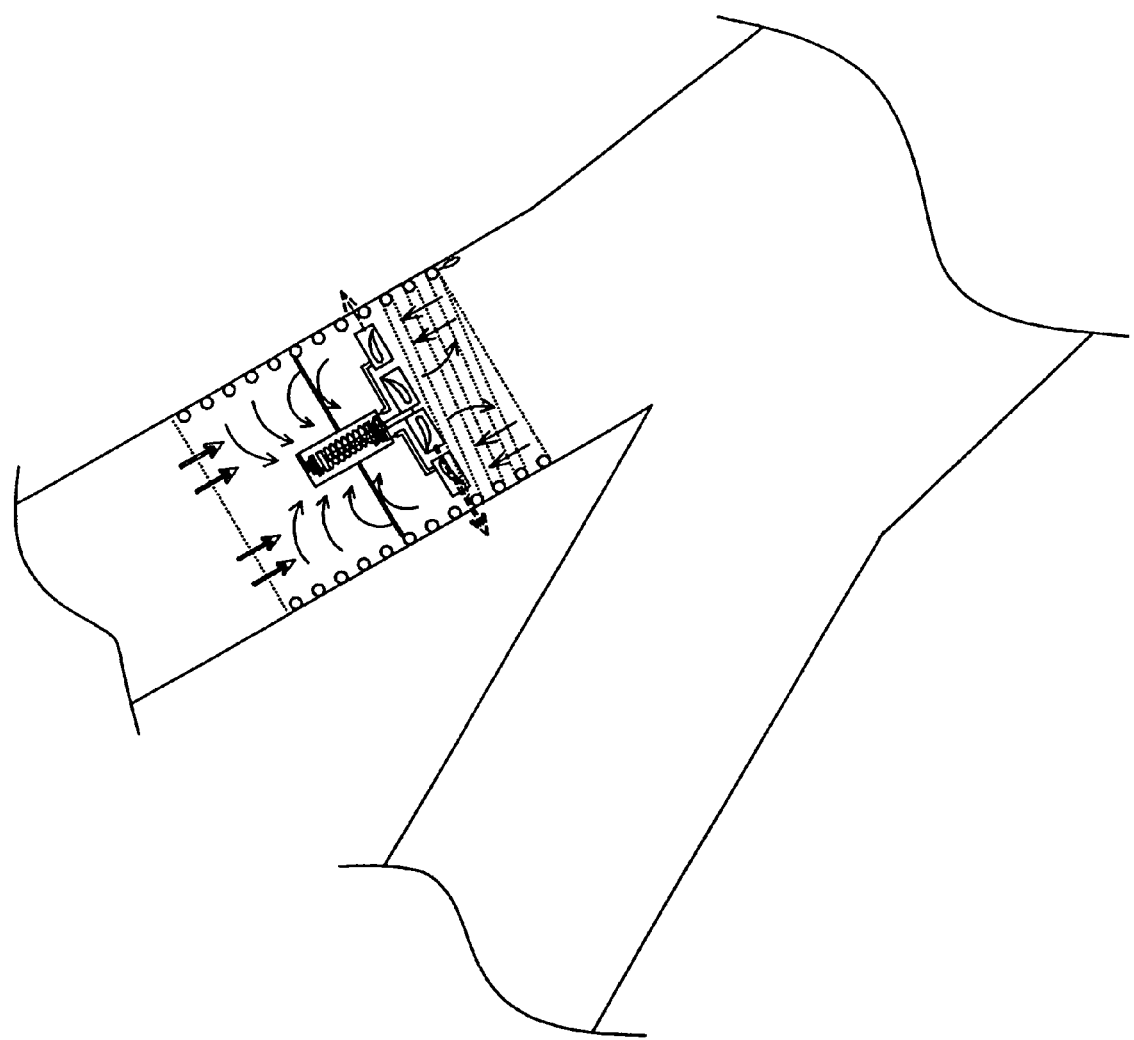

Reference is now made to FIGS. 3A-C, which are schematic illustrations of an endobronchial fluid exhaler that includes two separate but concentric propellers 16 and 17, in accordance with a third embodiment of the present invention. Typically, the propellers have airfoils which are angled in opposite directions to each other. In all other aspects, the third exhaler is generally similar to the first exhaler. Therefore, other embodiments of the exhaler that are described hereinabove with respect to the first inhaler and that also apply to the third exhaler are generally not repeated herein.

Compared with the first exhaler, the arrangement of propellers shown in FIGS. 3A-C typically enables the third exhaler to further hinder inhaled fluid 9 from entering the lung segment that is distal to the exhaler.

Only one of two concentric propellers 16 and 17 is typically linked to axis 2 during rotation of axis 2 in the direction of rotation 11 corresponding to the inhalation of fluid 9. Only the other of two concentric propellers 16 and 17 is typically linked to axis 2 during rotation of axis 2 in the direction of rotation 12 corresponding to the exhalation of fluid 10. Typically, the change in linking is implemented by a clutch mechanism 15.

Typically, placeholder 3 keeps axis 2, clutch mechanism 15 and propellers 16 and 17 positioned against the endobronchial lumen. Placeholder 3 is similar in form and function to the one described previously for the first exhaler.

The cross section (airfoil) of the blades of propeller 17 is typically unidirectional in the sense of making it more efficient in the direction of rotation 11 supporting the inhalation of fluid 9. The airfoil of the blades of propeller 16 is typically unidirectional in the sense of making it more efficient in the direction of rotation 12 supporting exhalation of fluid 10.

A main spring 4 interacts with axis 2. Main spring 4 is typically wound by the fluid 9 passing in the distal direction through propeller(s) 17 during the inhalation phases of the respiratory cycle. Inhaled fluid 9 typically causes the rotation of propeller(s) 1 in the inhalation direction 11, which in turn causes (via clutch mechanism 15) the rotation of axis 2, which in turn causes the winding of main spring 4. In some embodiments, given the inherent resistance created by the airways that are distal to the exhaler which are increasingly narrow and also potentially obstructed, some of fluid 9 may be turned back and flow via propeller 16 back toward the trachea. Propeller 16 is during that phase unlinked to axis 2 and may rotate freely.

Subsequently, once the inhalation phase of the respiratory cycle concludes and the exhalation phase begins, the energy accumulated in main spring 4 is released in the form of main spring 4 unwinding. Such unwinding causes the rotation of axis 2 in the exhalation direction 12, which unlocks clutch mechanism 15 from propeller 17 and locks it onto propeller 16, which causes the rotation of propeller 16 in the exhalation direction 12, which causes the exhalation of fluid 10 from the lung segment that is distal to the exhaler and toward the trachea. Typically, during that phase, propeller 17 is unlinked to axis 2 and may rotate freely.

Figure 4A:
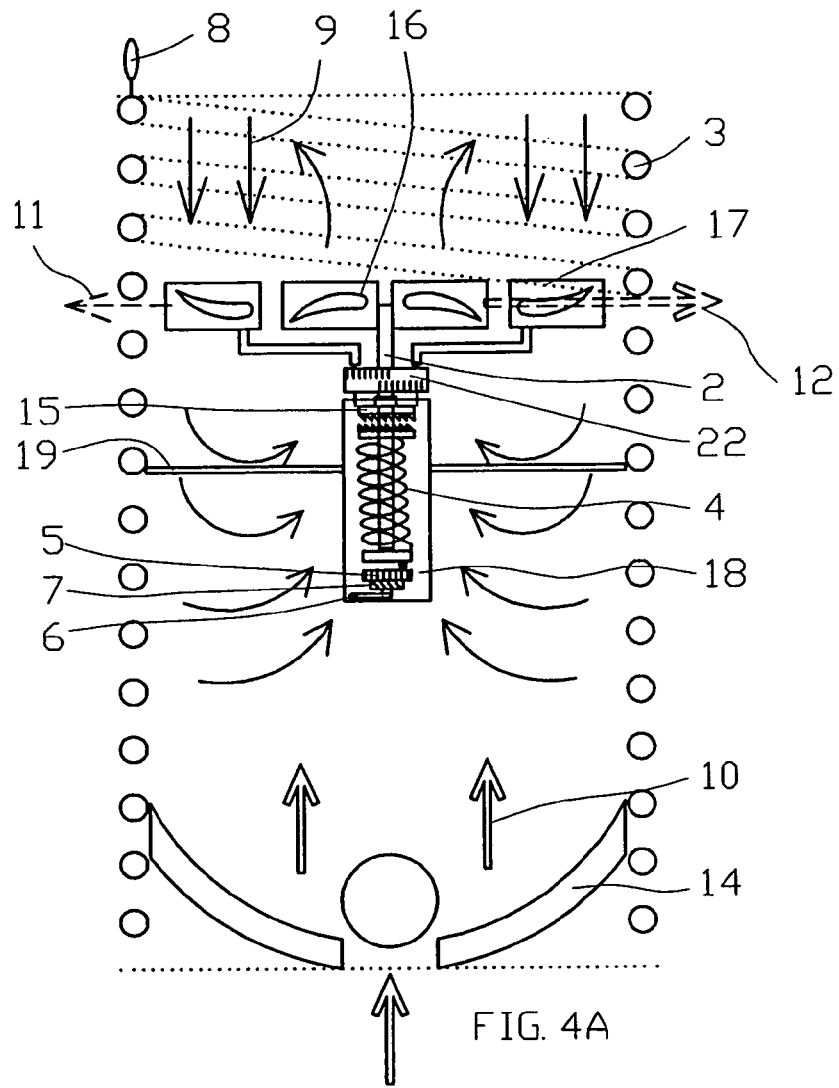
FIGS. 4A-C are schematic illustrations of an endobronchial fluid exhaler that includes two separate but concentric propellers and a unidirectional valve, in accordance with a fourth embodiment of the present invention.
Figure 4B:
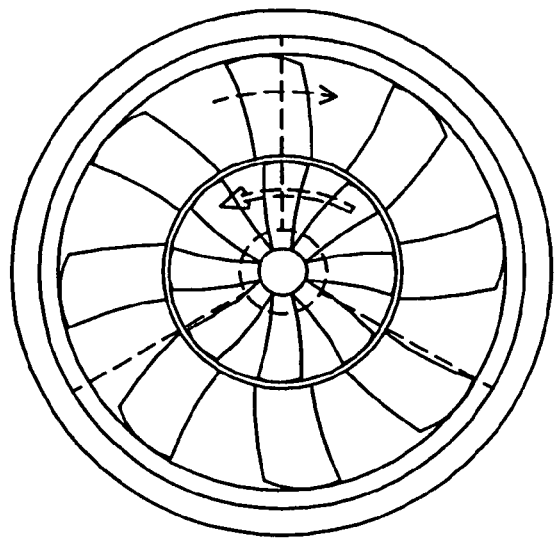
Figure 4C:
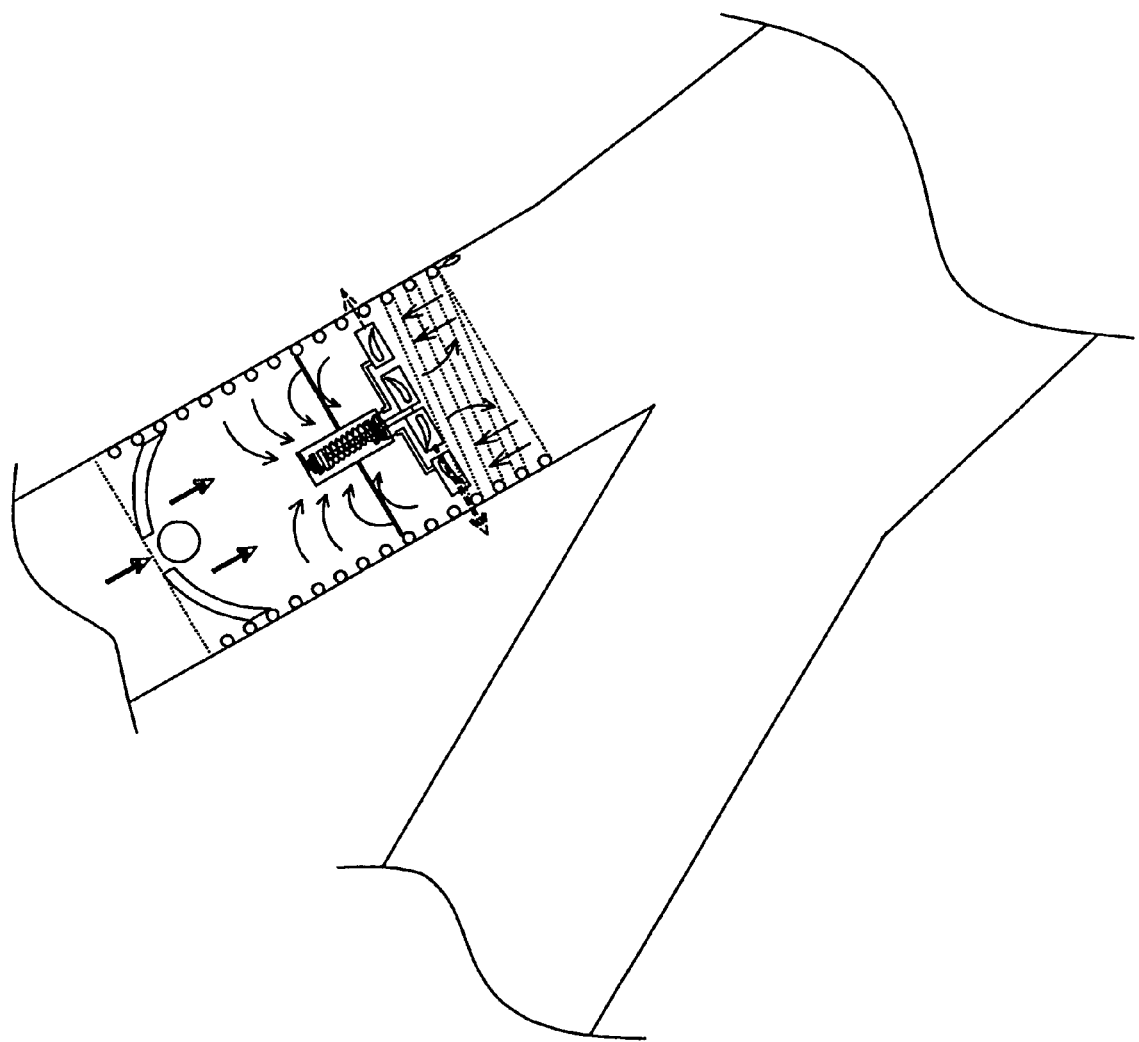

Reference is now made to FIGS. 4A-C, which are schematic illustrations of an endobronchial fluid exhaler that includes two separate but concentric propellers 16 and 17 and unidirectional valve 14, in accordance with a fourth embodiment of the present invention. The valve(s) typically further hinders, or prevents, the flow of fluid from the direction of the exhaler into the lung segment that is distal to the exhaler.

Figure 2A:
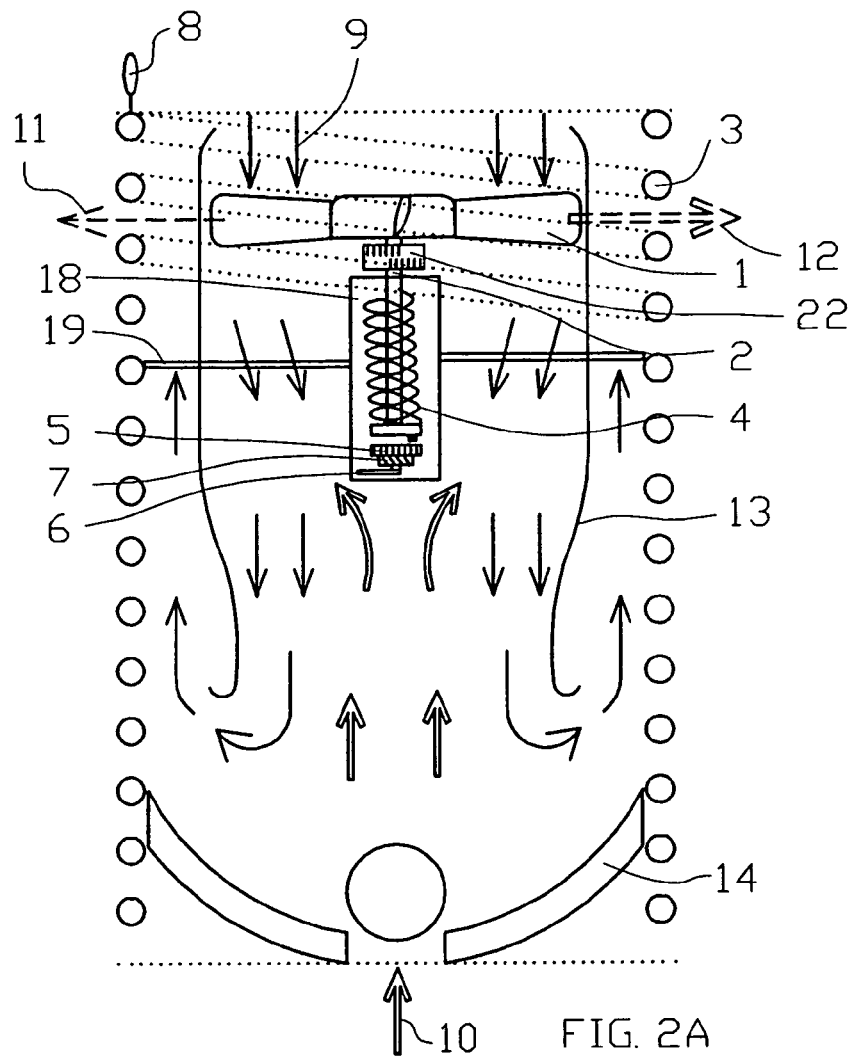
FIGS. 2A-C are schematic illustrations of an endobronchial fluid exhaler that includes (a) a unidirectional valve at its distal section, and (b) an inner tunnel, in accordance with a second embodiment of the present invention.
Figure 2B:
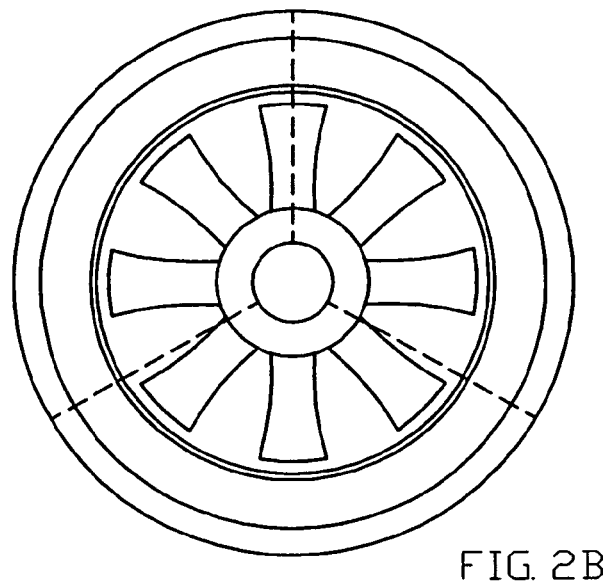
Figure 2C:
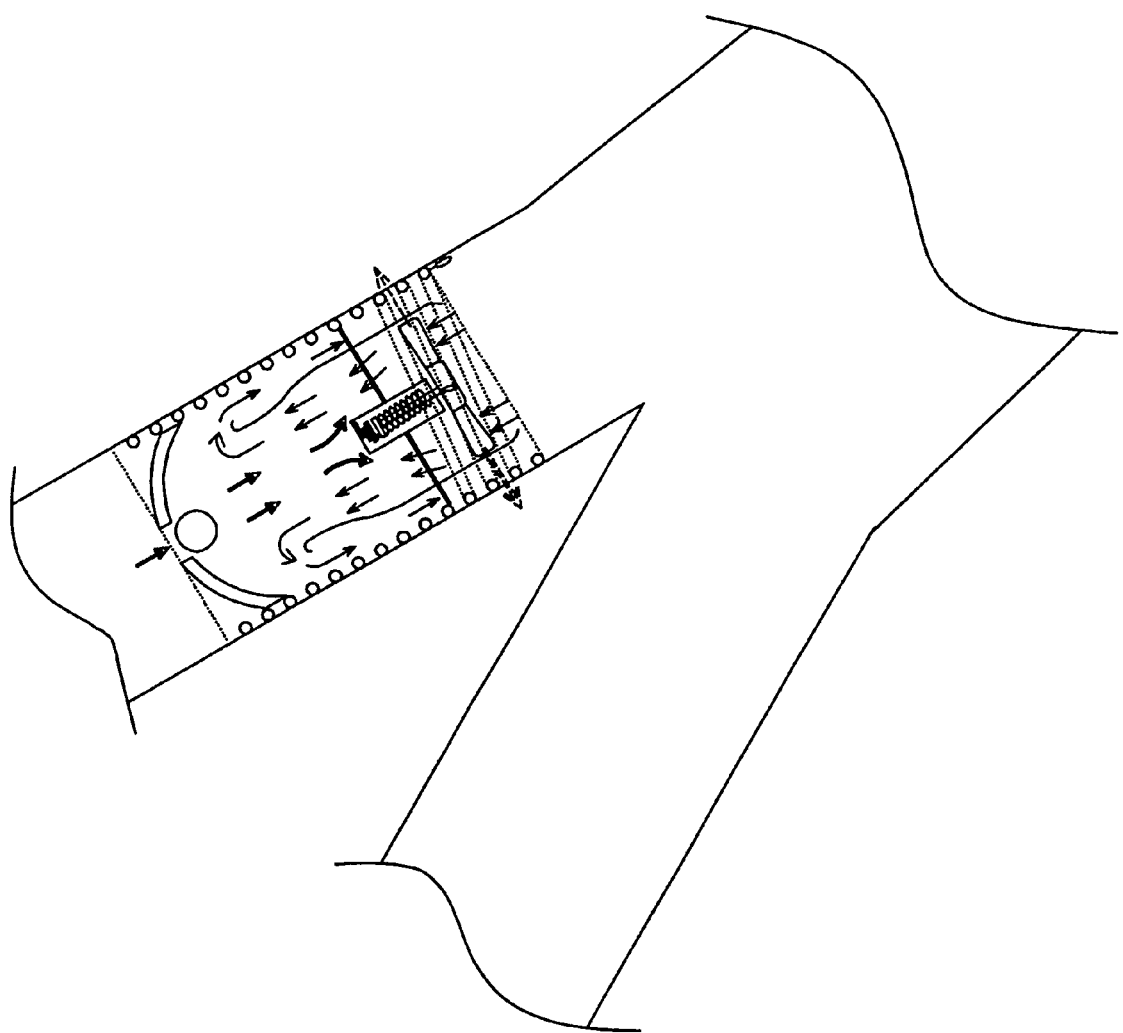

Other than valve(s) 14, this fourth exhaler is generally similar to the prior, third exhaler. Therefore, embodiments of the invention that are described with respect to the third exhaler that also apply to the fourth exhaler are generally not repeated herein. Unidirectional valve 14 is generally as described with respect to FIGS. 2A-C.

Figure 5:
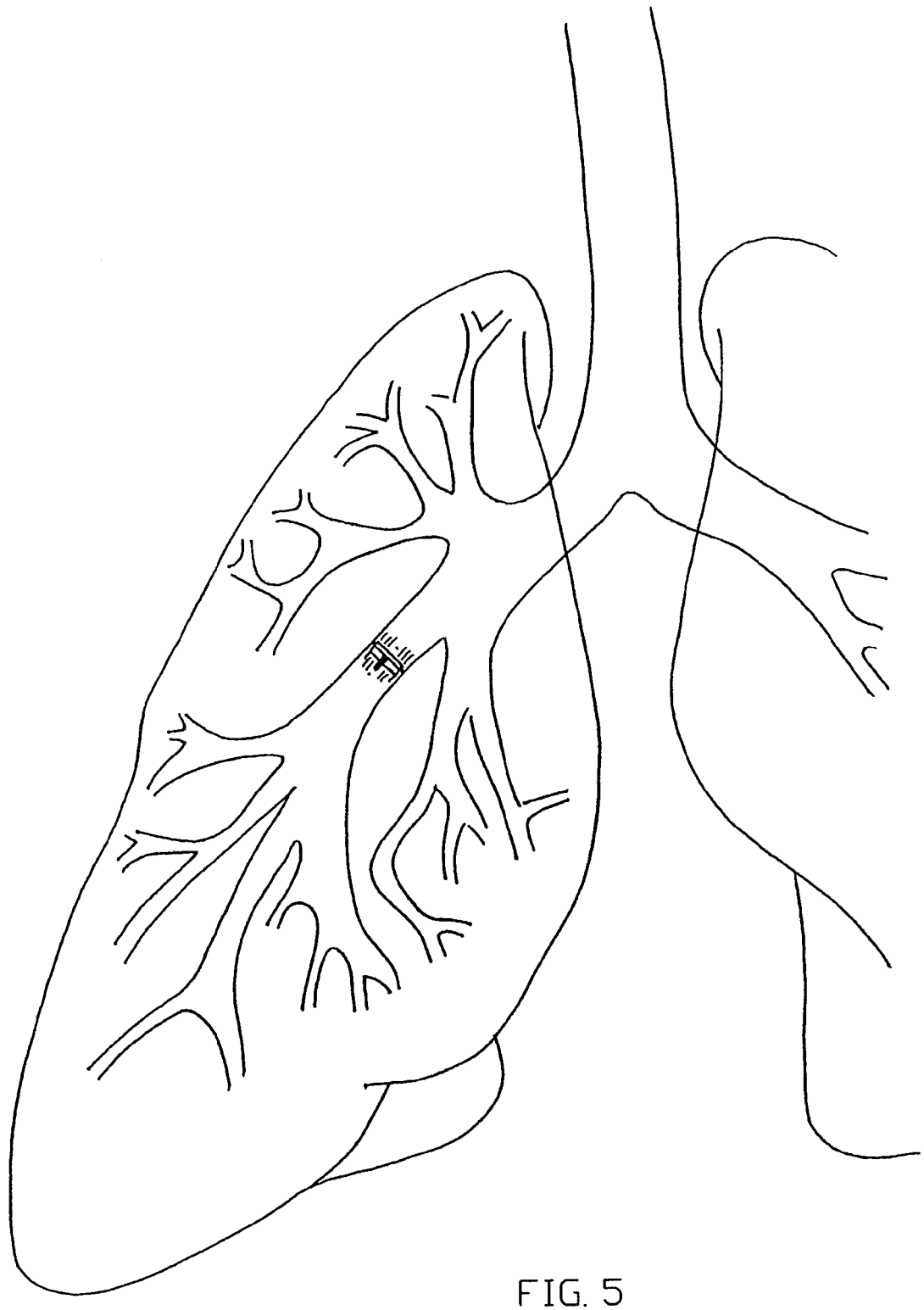
FIG. 5 is a schematic illustration of an endobronchial fluid exhaler placed within a bronchial airway, in accordance with an embodiment of the present invention.

Reference is now made to FIG. 5, which is a schematic illustration of an endobronchial fluid exhaler placed within a bronchial airway, in accordance with an embodiment of the present invention. In an alternative embodiment (not shown), the exhaler is placed at the trachea. In an embodiment, the exhaler is placed in an airway leading to a lung that is malfunctioning (e.g., an emphysematous lung) in whole or in part. In an embodiment, the exhaler is placed in an airway leading to a lobe that is malfunctioning (e.g., an emphysematous lobe) in whole or in part. In an embodiment, the exhaler is placed in an airway leading to a lobe segment that is malfunctioning (e.g., an emphysematous lobe segment) in whole or in part. In an embodiment, the exhaler is placed in an airway leading to a lobule that is malfunctioning (e.g., an emphysematous lobule) in whole or in part.

Figure 6A:
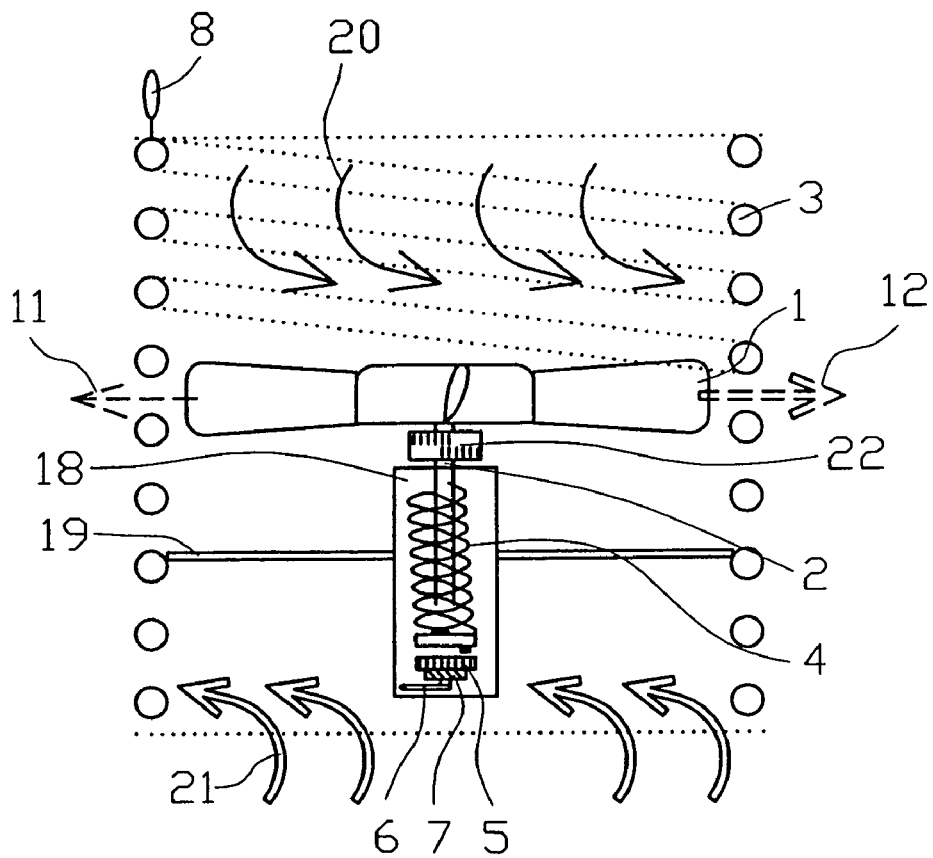
FIGS. 6A and 6B are schematic illustrations of a bronchial fluid exhaler in an airway in which the flow of fluid being inhaled and/or exhaled is not linear, in accordance with an embodiment of the present invention.
Figure 6B:
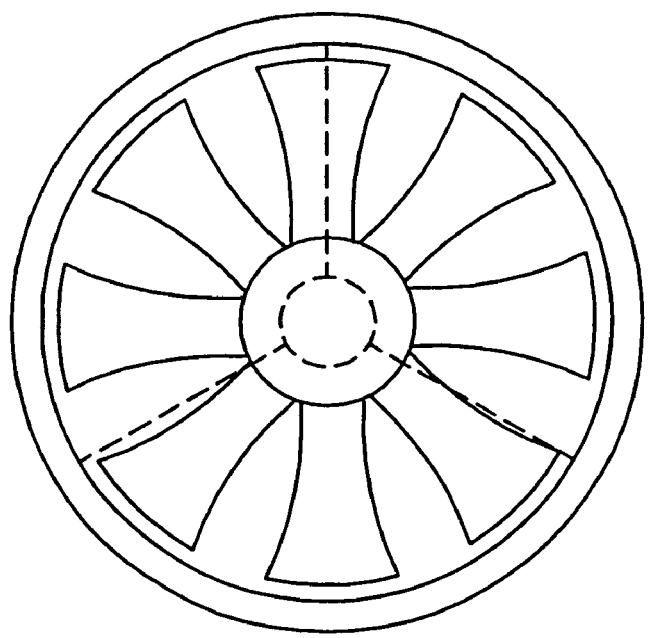

Reference is now made to FIGS. 6A and 6B, which are schematic illustrations of a bronchial fluid exhaler in an airway in which the flow of fluid being inhaled and/or exhaled is not linear, in accordance with an embodiment of the present invention. In some embodiments, the exhaler is placed in a circular or spiral flow of fluid. In such a case, the propeller(s) of the exhaler, in any of the aforementioned embodiments, may be more efficient in achieving their aforementioned functions. Specifically, inhaled fluid in direction 20 further rotates the propeller(s) and winds main spring 4, and/or exhaled fluid in direction 21 is further drawn by the propeller(s) when main spring 4 unwinds. This applies not only to the previously-disclosed first exhaler, but also to the second exhaler, the third exhaler and the fourth exhaler.

There is a growing body of knowledge indicating that the flow of fluid, particularly in the upper airways, is generally turbulent and often circular or spiral. (For example, see "Interactive Respiratory Physiology", Wilmot C. Ball Jr., MD, Johns Hopkins School of Medicine, Office of Medical Informatics Education, 1996). Other research has claimed that turbulent flow may exist anywhere in the lungs, for example, as described in an article by Tsuda et al., entitled "Chaotic mixing deep in the lung," Proceedings of the National Academy of Sciences of the USA, July 2002.

Curschmann's spirals, originally discovered in the 19th century, are condensed twists of mucus observed in asthma patients that indicate spiral flows, for example, see "Sputum Induction in Asthma" by Brightling, Chest 2006, and "Pathology of Asthma and COPD" by P. Jeffery, Cambridge University Press, 2003.

Recent research conducted by H. Becker at Thoraxklinik Heidelberg, Germany, indicates that (as observed by Vibration Response Imaging) the flow of exhaled fluid is generally spiral and not linear, and that in the vast majority of patients the direction of the spiral is counterclockwise when looked upon from proximal to distal.

All of the aforementioned references are incorporated herein by reference.

In an embodiment, the exhaler is provided in two configurations with respect to directions of rotation. In the first configuration, the propeller(s)' direction of rotation 11 during inhalation is clockwise while the direction of rotation 12 during exhalation is counterclockwise. In the second configuration, the propeller(s)' direction of rotation 11 during inhalation is counterclockwise while the direction of rotation 12 during exhalation is clockwise.

In an embodiment, prior to implantation of the exhaler, a subject goes through functional imaging (such as Vibration Response Imaging) that examines which of these two exhaler configurations is more suitable for the specific subject. Subsequently, a configuration where the propeller(s)' directions of rotation offer the best match with the directionality of the naturally-induced flow of fluid within that subject's lungs is selected.

Separately, in an embodiment, the desired location(s) for the placement of an exhaler are determined with the help of a software package that assists in analyzing lung images of a subject and identifying emphysematous regions. Such software packages include, for example, the Pulmonary Workstation and the Emphysema Profiler, both from Vida Diagnostics of Iowa City, Iowa, USA.

Any of the embodiments of an endobronchial fluid exhaler described above may also comprise an opening which is normally closed and may be opened with the help of a probe inserted into the airways. Such an opening may comprise, for example, a lid, a valve, a membrane, a diaphragm, or any combination thereof. The opening may be used in cases where a probe needs to be inserted into the lung area situated distally to the fluid exhaler. Such probes may comprise any diagnostic or therapeutic probe, including but not limited to a biopsy probe, a navigational probe, a sheath, a guide wire, a suction probe, a washing (lavage) probe, an ablation probe, a tissue characterization probe, a fluid characterization probe, a substance delivery probe, an imaging probe, or any combination thereof.

In an embodiment, the opening is implemented through a lumen within axis 2. In an embodiment, the inherent synchronization of axis 2 with the respiratory cycle (i.e., it rotates in direction 11 only during inhalation and in direction 12 only during exhalation) is used for closing and opening the opening in synchronization with the respiratory cycle. In an embodiment, such synchronization is used for dispensing a medication through the opening in synchronization with the respiratory cycle.

In an embodiment, the opening is implemented in any other endobronchial device intended to ameliorate lung emphysema or other forms of COPD. In an embodiment of the invention, an opening as described above is implemented in other endobronchial devices.

In an embodiment, multiple endobronchial fluid exhalers are implanted in multiple airways leading to multiple emphysematous regions, as in the case of diffuse emphysema.

Embodiments of the current invention also includes several methods for inserting the endobronchial fluid exhaler(s) into the airway(s) leading to the emphysematous regions. A first method of insertion and placement comprises the following steps:

(i) A guidewire is inserted via a bronchoscope to the desired point of placement of the device within the airway;

(ii) The guidewire is kept in place with its distal segment positioned at the desired point of placement while the bronchoscope is retrieved;

(iii) The fluid exhaler is inserted along the guidewire until it reaches the desired point of placement;

(iv) Placeholder portion of the fluid exhaler is expanded such that the fluid exhaler is anchored in place against the airway wall;

(v) The guidewire is retrieved.

A second method of inserting and placing the fluid exhaler(s) avoids the retrieval of the bronchoscope prior to inserting the device to the desired point of placement. For example, placement of the fluid exhaler may be performed under direct bronchoscopic vision (which is typically an additional advantage). When using this second method, the fluid exhaler being inserted via the bronchoscope is constructed such that during insertion it is collapsed into an outer diameter that is considerably smaller than its final diameter once it is placed in the desired position and expanded. The diameter of the exhaler when it is in its collapsed form is typically sufficiently small to fit within the inner diameter of the working channel of a commonly-used bronchoscope. In an embodiment, the exhaler is inserted through a sheath that is inserted through the bronchoscope's channel. In an embodiment, the sheath or parts thereof are transparent, so that the exhaler can be imaged by the endoscope once the sheath protrudes out of the bronchoscope's channel. In an embodiment, the sheath comprises radiopaque markers at or toward its distal tip, to facilitate its identification under fluoroscopic imaging.

In an embodiment, a third method of inserting the fluid exhaler(s) utilizes a probe that is inserted through the airways not through an endoscope.

In an embodiment, a fourth method is used with an exhaler that comprises arms 19 that are detachable. In such a case, placeholder 3, in an embodiment wherein it is collapsible and expandable, is inserted through the channel of the endoscope in the aforementioned second method of insertion in a collapsed form and expanded once it is in position. Subsequently, other components of the exhaler are inserted in the aforementioned first or third methods not through an endoscope. Those other components are then placed within placeholder 3, which is already implanted at that time, and become connected to it by arms 19.

In an embodiment, a fifth method is used with an exhaler that comprises arms 19 that are detachable. In such a case, placeholder 3, in an embodiment wherein it is collapsible and expandable, is inserted through the channel of the endoscope in the aforementioned second method of insertion in a collapsed form and expanded once it is in position. Subsequently, the other components of the exhaler, also in an embodiment wherein they are collapsible and expandable, are also inserted through the channel of the endoscope in the aforementioned second method of insertion in a collapsed form. Those other components are then placed within placeholder 3 which is already implanted at that time, expanded, and become connected to placeholder 3 by arms 19.

In an embodiment, a navigation system is used when inserting, placing or removing the fluid exhaler(s). In an embodiment, the navigation system comprises a navigated probe, one or more location sensor(s) coupled to the navigated probe, and an image of bronchial airways on which the location of the navigated probe is superimposed. In an embodiment, the image is pre-operative, (i.e., generated prior to the insertion or removal of the fluid exhaler), and/or intra-operative (i.e., generated during the insertion or removal of the fluid exhaler). In an embodiment, the location sensor(s) is magnetic, electromagnetic, ultrasonic, optical, radioactive or any combination thereof. In an embodiment, the image is generated by sources comprising ionizing radiation, non-ionizing radiation, X-Ray, fluoroscopy, ultrasound, CT, PET, SPECT, PET-CT, MRI, Optical Imaging, Optical Coherence Tomography, infra-red imaging, Vibration Response Imaging, other forms of Functional Imaging, or any combination thereof. When using this method, the location of the navigated probe is provided by the location sensor(s) and shown during the procedure superimposed on the images. In an embodiment, the navigated probe is coupled to the fluid exhaler and used to insert, place or remove the fluid exhaler itself. For some applications, the navigated probe is also used to insert, place or remove a second probe, with the fluid exhaler coupled to the second probe and not to the navigated probe itself.

In an embodiment, the navigation system is used for the insertion, placement or removal of any other endobronchial device intended to ameliorate lung emphysema.

In an embodiment, explanation of the fluid exhaler(s) is achieved by contracting the exhaler to separate placeholder 3 from the endobronchial wall against which it is situated. This is typically followed by the removal of the entire exhaler through the bronchial airways and through the trachea.

Alternatively, in embodiments wherein arms 19 are detachable, most components of the exhaler can be removed from the subject's body while placeholder 3 remains implanted in place. In some embodiments, this method is used if the exhaler has been implanted for some period, during which placeholder 3 has already become attached to or within the tissue of the endobronchial wall.

Optionally, and in conjunction with either of the above insertion and placement methods, a separate unidirectional valve of the type described in U.S. Pat. Nos. 6,679,264 and 6,694,979 to Deem et. al., or in U.S. Pat. Nos. 6,258,100 and 6,293,951 to Alferness et. al., both of which are cited hereinabove, may also be placed in the airway separately, distally or proximally to the fluid exhaler(s).

While embodiments of the current invention are described primarily with respect to the respiratory system, the aforementioned underlying principles of energy accumulation and release may also be applied to other bodily systems, such as the cardiovascular system and the urinary system.

In an embodiment, the flow of blood in the cardiovascular system, and/or the contraction and expansion of the heart muscle, and/or the motion of the aorta, is utilized for the accumulation of energy that is later used for powering intra-body sensors including without limitation a pressure sensor, a flow sensor, a temperature sensor, an impedance sensor, a fluid composition sensor, an electrical activity sensor, an electrical conductivity sensor, a signal propagation sensor, a chemical analysis sensor, or any combination thereof. Such accumulation of energy may be by a propeller rotated by the flow of blood, or by a spring contracted and expanded by the motion of the heart, muscle, and/or the aorta, etc.

In some embodiments, the flow of blood in the cardiovascular system, and/or the contraction and expansion of the heart muscle, and/or the motion of the aorta, is utilized for the accumulation of energy that is later used for powering an intra-body cardiac device such as a pacemaker or a defibrillator. For some applications, the accumulation of energy is by means of a propeller rotated by the flow of blood, or by a spring contracted and expanded by the motion of the heart muscle or the aorta or another cardiovascular site. Typically, but not necessarily, energy from the cardiovascular system is stored during more than one cycle, and subsequently released on one or more cycles.

In an embodiment, the flow of urine in the urinary system utilized for the accumulation of energy that is later used for powering intra-body sensors, including without limitation, a pressure sensor, a flow sensor, a temperature sensor, an impedance sensor, a fluid composition sensor, an electrical conductivity sensor, a signal propagation sensor, a chemical analysis sensor, or any combination thereof. Such accumulation of energy may be by a propeller rotated by the flow of urine, or by the change in size of, for example, the bladder.

All of the above-listed references are incorporated herein by reference.

Although embodiments of the invention have been described in which a propeller is rotated to extract energy, the scope of the invention is not limited to the use of a propeller but encompasses the use of any rotating member. Similarly, although embodiments of the invention have been described in which a spring is wound to store energy, the scope of the invention is not limited to the use of a spring but encompasses the use of any device that is configured to accumulate energy via the rotation of a rotating member, i.e., any energy accumulator.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
    extracting mechanical energy from a flow of fluid during inhalation of the flow of fluid by a subject; storing the extracted energy in an airway of the subject; releasing the energy when the subject exhales; wherein extracting the mechanical energy comprises extracting mechanical energy during N inhalations of the subject, and wherein releasing the energy comprises releasing the energy during fewer than N exhalations of the subject.

2. The method according to claim 1, wherein releasing the energy comprises assisting exhalation of the subject in synchronization with a respiratory cycle of the subject.

3. The method according to claim 1, further comprising inserting an energy extractor into an airway of the subject, the energy extractor being configured to extract the energy from the inhaled flow of fluid.

4. The method according to claim 3,
    wherein the energy extractor includes at least an expansible portion, and
    wherein inserting the energy extractor comprises:
        inserting an expansible structure into the airway,
        expanding the expansible structure,
        inserting the expansible energy extractor into the airway, and
        coupling the energy extractor to the expansible structure by expanding the expansible portion of the energy extractor.

5. The method according to claim 3, wherein inserting the energy extractor comprises expanding an expansible structure that is coupled to the energy extractor while the energy extractor is within the airway.

6. The method according to claim 5, further comprising contracting the expansible structure and removing the expansible structure and the energy extractor from the airway subsequent to the contracting.

7. The method according to claim 5, further comprising inserting a bronchoscope into the airway, wherein inserting the energy extractor comprises inserting the energy extractor via the bronchoscope, and wherein expanding the structure comprises expanding the structure while the bronchoscope is within the airway.

8. The method according to claim 3, wherein inserting the energy extractor comprises:
   inserting an expansible structure into the airway,
   expanding the expansible structure,
   inserting the energy extractor into the airway, and
   coupling the energy extractor to the expansible structure.

9. The method according to claim 1, further comprising extracting energy from motion of a portion of the subject's body.

10. The method according to claim 1, wherein storing the extracted energy comprises winding a spring, and wherein releasing the stored energy comprises unwinding the spring.

11. The method according to claim 1, further comprising detecting a phase of a respiratory cycle of the subject, wherein extracting the mechanical energy comprises extracting mechanical energy in synchronization with the respiratory cycle and wherein releasing the energy comprises releasing energy in synchronization with the respiratory cycle.

12. A method for use with a portion of a subject's body that undergoes cyclical motion due to a respiratory cycle of the subject, the method comprising: extracting mechanical energy from the motion of the portion of the subject's body over a period of time in which the portion undergoes N respiratory cycles, N being two or more; storing the extracted energy; releasing the energy during fewer than N cycles; wherein extracting the mechanical energy comprises extracting mechanical energy from a flow of fluid through the subject's body.

13. The method according to claim 12, wherein extracting the mechanical energy comprises extracting mechanical energy from a flow of fluid through an airway of the subject.

14. A method comprising: extracting mechanical energy from a flow of a fluid within a subject's body; powering an electrical sensor that is implanted in the subject's body using the extracted energy; storing the extracted energy in an airway of the subject; releasing the energy when the subject exhales; wherein extracting the mechanical energy comprises extracting mechanical energy during N inhalations of the subject, and wherein releasing the energy comprises releasing the energy during fewer than N exhalations of the subject.

15. The method according to claim 14, wherein extracting the mechanical energy comprises extracting mechanical energy by rotating a rotating member.

* * * * *